(12) United States Patent
Van Der Zaag et al.

(10) Patent No.: US 9,568,464 B2
(45) Date of Patent: Feb. 14, 2017

(54) MANUFACTURING METHOD OF AN APPARATUS FOR THE PROCESSING OF SINGLE MOLECULES

(71) Applicant: KONINKLIJKE PHILIPS N.V., Eindhoven (NL)

(72) Inventors: Pieter Jan Van Der Zaag, Waalre (NL); Emiel Peeters, Eindhoven (NL); Roelof Koole, Eindhoven (NL); Falco Cornelius Marinus Jacobus Maria Van Delft, Dommelen (NL)

(73) Assignee: Koninklijke Philips N.V., Eindhoven (NL)

( * ) Notice: Subject to any disclaimer, the term of this patent is extended or adjusted under 35 U.S.C. 154(b) by 33 days.

(21) Appl. No.: 14/385,398

(22) PCT Filed: Mar. 14, 2013

(86) PCT No.: PCT/IB2013/052026
§ 371 (c)(1),
(2) Date: Sep. 15, 2014

(87) PCT Pub. No.: WO2013/140316
PCT Pub. Date: Sep. 26, 2013

(65) Prior Publication Data
US 2015/0027980 A1    Jan. 29, 2015

Related U.S. Application Data

(60) Provisional application No. 61/614,051, filed on Mar. 22, 2012.

(30) Foreign Application Priority Data

Jun. 29, 2012   (EP) ..................................... 12174261

(51) Int. Cl.
B44C 1/22        (2006.01)
G01N 33/487      (2006.01)
(Continued)

(52) U.S. Cl.
CPC ..... G01N 33/48721 (2013.01); B81C 1/00087 (2013.01); B82Y 30/00 (2013.01); G03F 7/0002 (2013.01); B81C 2201/0149 (2013.01)

(58) Field of Classification Search
CPC ............... H01L 21/31138; H01L 21/31144; H01L 21/312; H05K 3/048; H05K 3/061; H05K 3/064; B81C 1/0008; B81C 2201/0149; B82Y 30/00
(Continued)

(56) References Cited

U.S. PATENT DOCUMENTS 8,263,323 B2 *  9/2012 Yoon et al. ................... 430/324
8,623,458 B2 *  1/2014 Cheng et al. ................. 427/259
(Continued)

FOREIGN PATENT DOCUMENTS

WO    2011046706 A1    4/2011

OTHER PUBLICATIONS

Emiel Peeters et al, "Block copolymer self-assembly; Extension of lithography to 22nm node and beyond", ASML.
(Continued)

Primary Examiner — Lan Vinh

(57) ABSTRACT

The invention relates to a method for manufacturing an apparatus for the processing of single molecules. According to this method, a self-assembling resist (155) is deposited on a processing layer (110, PL) and allowed to self-assemble into a pattern of two phases (155a, 155b). One of these phases (155a) is then selectively removed, and at least one aperture is generated in the processing layer (110, PL) through the mask of the remaining resist (155b). Thus
(Continued)

apertures of small size can readily be produced that allow for the processing of single molecules (M), for example in DNA sequencing.

13 Claims, 20 Drawing Sheets

(51) Int. Cl.
    *G03F 7/00*     (2006.01)
    *B82Y 30/00*     (2011.01)
    *B81C 1/00*     (2006.01)

(58) Field of Classification Search
    USPC ...... 216/17, 40, 41, 47, 49, 79, 81; 438/725, 438/736; 430/313, 324, 325
    See application file for complete search history.

(56) References Cited

U.S. PATENT DOCUMENTS

| | | | |
|---|---|---|---|
| 8,734,904 B2* | 5/2014 | Cheng | H01L 21/0337 427/256 |
| 8,879,158 B2* | 11/2014 | Choi et al. | 359/642 |
| 2004/0229386 A1 | 11/2004 | Golovchenko et al. | |
| 2008/0299353 A1* | 12/2008 | Stoykovich et al. | 428/195.1 |
| 2008/0311375 A1* | 12/2008 | Harnack et al. | 428/315.7 |
| 2009/0308837 A1* | 12/2009 | Albrecht et al. | 216/22 |
| 2010/0178615 A1* | 7/2010 | Colburn | B81C 1/00031 430/323 |
| 2010/0327847 A1 | 12/2010 | Leiber et al. | |
| 2011/0147983 A1* | 6/2011 | Cheng | B81C 1/00031 264/220 |
| 2011/0147985 A1* | 6/2011 | Cheng et al. | 264/225 |
| 2012/0037919 A1 | 2/2012 | Xu et al. | |

OTHER PUBLICATIONS

Jingwei Bai et al, "Graphene nanomesh", Nature Nanotechnology, vol. 5, 14, Feb. 14, 2010, pp. 190-194, XP002714559.
Henk W. Ch. Postma, "Rapid Sequencing of Individual DNA Molecules in Graphene Nanogaps", Nano Letters, 10, pp. A-F.
K.S. Novoselov et al, "Electric Field Effect in Atomically Thin Carbon Films", Science, 306, Oct. 22, 2004, pp. 666-669.
D. Malko et al, "Competition for graphene: Graphynes with direction-dependent dirac cones", Phys. Rev. Lett. 108, 086804, Feb. 24, 2012.

* cited by examiner

MANUFACTURING METHOD OF AN APPARATUS FOR THE PROCESSING OF SINGLE MOLECULES

CROSS-REFERENCE TO PRIOR APPLICATIONS

This application is the U.S. National Phase application under 35 U.S.C. §371 of International Application Serial No. PCT/IB2013/052026, filed on Mar. 14, 2013, which claims the benefit of U.S. Provisional Patent Application Ser. No. 61/614,051 filed on Mar. 22, 2012 and European Patent Application No. 12174261.3, filed on Jun. 29, 2012. These applications are hereby incorporated by reference herein.

FIELD OF THE INVENTION

The invention relates to a method for manufacturing an apparatus that can be used for the processing of single molecules.

BACKGROUND OF THE INVENTION

The US 2010/0327847 A1 discloses a solid state molecular sensor having an aperture extending through a graphene layer. A change in an electrical characteristic of said layer is measured when a molecule passes through said aperture. One drawback of this sensor is the high electrical conductivity of the graphene layer, compared to which conductivity changes induced by a molecule are very small.

Furthermore, it has been described in literature (H. W. Ch. Postma, "Rapid sequencing of individual DNA molecules in graphene nanogaps", Nano Lett. 10 (2010) 420-425) that a DNA molecule can be sequenced by passing it through a gap between two graphene layers. The associated apparatus is, however, mechanically not very robust as free graphene layers are used. Moreover, the comparatively long gap between said layers allows long molecules to pass it with many different orientations and configurations, making the interpretation of measurement results difficult.

SUMMARY OF THE INVENTION

It is an object of the invention to provide improved means for the processing of single molecules, particularly for the sequencing of nucleic acids like DNA.

This object is achieved by a manufacturing method according to claim 1 and an apparatus according to claim 14. Preferred embodiments are disclosed in the dependent claims.

The method according to the present invention serves for the manufacturing of an apparatus with which single molecules (or atoms) can be processed, particularly macromolecules like proteins or nucleic acids. In this context, the term "nucleic acids" shall most generally comprise molecules (e.g. DNA, RNA) that contain naturally and/or non-naturally occurring nucleotides or modifications thereof as well as LNA (locked nucleic acids) and PNA (peptide nucleic acids). The "processing" of these molecules may comprise their physical and/or chemical transformation or alternation. In many important applications, the processing will however be a sensing, particularly serving for the detection of different sections of a molecule. Thus it may for example be possible to sequence ss-DNA, ds-DNA or the like.

The manufacturing method comprises the following steps, which are preferably executed in the listed order, but which may also be executed in any other order that is appropriate:

a) Providing a layer of a (solid) material. This layer will in the following for purposes of reference be called "processing layer" (indicating that it is further processed in the manufacturing procedure and that it takes part in the processing of single molecules in the accomplished apparatus).

The processing layer may optionally comprise two or more sub-layers of different materials and/or structures. Moreover, the processing layer may be homogenous or (e.g. geometrically or chemically) structured. As the term "layer" indicates, the processing layer will typically have a sheet-like geometry with a width and length that are considerably larger than its thickness.

b) Depositing a material on the aforementioned processing layer (i.e. on an outer surface thereof), wherein said material shall have the feature to self-assemble into a pattern of (at least) two different regions of different (chemical and/or physical) composition and wherein at least one of these regions can selectively be removed. Due to these properties, said material will in the following be called "self-assembling resist". Moreover, a region with a particular composition will be called a "phase" of the self-assembling resist, i.e. said resist assembles into a pattern of at least two different phases (in the sense of the present invention) of which at least one can selectively be removed. After its deposition, said self-assembling resist is allowed to self-assemble into its associated pattern of phases.

c) Removing selectively (at least) one phase of the aforementioned self-assembling resist, leaving behind a pattern of the other phase(s). The removal may for example be done by selective etching.

d) Generating at least one aperture in the processing layer through the mask that is provided by the remaining self-assembling resist, wherein said aperture is such that it allows for the passage of single molecules in the accomplished apparatus. The aperture may for example be generated by etching the processing layer with an etchant that does not affect the remaining phase(s) of the self-assembling resist.

The described method has the advantage that it allows for the generation of small apertures by which single molecules can reliably be processed. This is achieved by exploiting the self-assembling characteristics of certain resists, which yield structures of nanometer-sizes that are appropriate for the intended purposes. At the same time, the manufacturing method allows for a mass production because a multitude of apertures can be generated in parallel this way. This is a considerable advantage over production methods as for example e-beam lithography by which apertures of comparable small sizes can only be produced sequentially.

After the generation of the at least one aperture in the processing layer, there is still the mask of the self-assembling resist on the processing layer. According to one embodiment of the invention, this residual resist is left where it is, serving for example as an electrical insulation. According to another embodiment of the invention, the manufacturing method comprises the additional step "e)" of removing the remaining self-assembling resist from the processing layer. In this case, the self-assembling resist serves solely as an intermediate mask during the production of the apparatus.

The processing layer may optionally be pre-treated before the deposition of the self-assembling resist in step b), wherein this pre-treatment is such that it affects the resulting pattern of phases that is formed by the self-assembling resist. Thus the formation of the pattern can be controlled or adjusted as required.

The aforementioned pre-treatment may for example comprise the provision of the processing layer with a particular (optionally structured) surface chemistry. According to a preferred embodiment, the pre-treatment of the processing layer comprises the deposition of a resist on the processing layer and the patterning of this resist. For the purpose of reference, this resist will in the following be called "primary resist". With the patterning of the primary resist, confined areas like trenches or holes may for example be generated on the surface of the processing layer in which the self-assembling resist can develop specific patterns of phases. The primary resist may thus serve as a kind of framework or matrix for the self-assembling resist.

The aforementioned patterning of the primary resist may particularly be done by optical lithography and/or by e-beam lithography. Optical lithography advantageously allows for the parallel processing of large areas in one step, providing them with a coarse structure to which the self-assembling resist can later add a fine structure.

According to a further development of the invention, the steps b), c), and d)—i.e. the deposition of a self-assembling resist, the removal of one phase of this resist, and the generation of at least one aperture—may be executed a first time with respect to a first processing layer and a second time with respect to a second processing layer, wherein said first and second processing layers may be identical or different. Optionally, further related steps, e.g. the removal of remaining self-assembling resist and/or the deposition of a (structured) primary resist, may be repeated, too. When the processing steps are executed with the same processing layer, this will result in the generation of apertures in said layer according to the different patterns of the applied two self-assembling resists. When the processing steps are executed with different processing layers, the resulting apertures will be located in different layers and may optionally also have different patterns.

In a particular realization of the aforementioned embodiment, the second processing layer comprises the first processing layer. This entails that the later produced apertures will also penetrate the first processing layer that comprises already the first produced apertures.

In another realization of the above embodiment, there may be the intermediate additional step of depositing a new layer of material onto the first processing layer (which has already been structured in first steps a)-d)), wherein this new layer is comprised by the second processing layer that is structured in second steps b)-d) next.

The patterns of the self-assembling resists that are applied in the first and the second execution of the above steps may preferably be different in alignment and/or geometry. This allows for the generation of elaborate aperture structures.

According to a preferred realization of the aforementioned embodiment, the first and the second pattern each comprise stripes of (at least) one phase, wherein the stripes of the different patterns are oblique to each other. The apertures that are generated with the self-assembling resists will then be oblique slits. Preferably, the oblique slits are in different layers and overlap, thus commonly constituting a smaller aperture in the region of their overlap.

In general, the pattern that is generated by the phases of the self-assembling resist may comprise stripes or cylinders of one phase. Stripes allow for the generation of trenches, while cylinders enable the generation of round holes in the processing layer.

In another preferred embodiment of the invention, the self-assembling resist may comprise a block copolymer. The macromolecules of the self-assembling resist then consist of two (or more) monomers, wherein sections consisting of only one type of monomer constitute "blocks" and wherein different blocks alternate. By a proper choice of the monomers, the corresponding blocks will have particular chemical and/or physical properties that enable the (self-) arrangement of the macromolecules in specific patterns.

The processing layer may particularly comprise a non-conductive sub-layer or material, for example $SiO_2$, $SiN_x$ or h-BN. Additionally or alternatively, it may comprise an electrically conductive sub-layer or material.

The aforementioned electrically conductive sub-layer or material may particularly comprise graphene or from graphene derived materials such as graphyne (cf. D. Malko, C. Neiss, F. Vinesc, and A. Görling, Phys Rev. Lett. 108, 086804 (2012)). Graphene (or a derivative) is a preferred material due to its favorable electrical and mechanical properties at nano-scale dimensions. The graphene (or its derivative) may be present in five monolayers or less, preferably two monolayers, or more preferably in a single monolayer. Thus a favorable low thickness can be achieved.

According to a further development of the invention, an additional layer may be deposited at least partially on the processing layer, wherein said additional layer may particularly be a conductive or a non-conductive layer. An additional layer may be advantageous in that it increases the mechanical stability, provides an electrical insulation (if it is non-conductive), and helps to orient processed single molecules appropriately. Moreover, an additional layer may constitute a further processing layer or a part thereof in a further application of the structuring steps of the invention.

Depending on the intended processing of the single molecules, additional components of the apparatus may be needed. Such components may particularly be realized by an electrical circuit adapted to control interactions with the molecules passing through the aperture. Such a circuit is preferably connected to the processing layer and/or a sub-layer thereof. In addition, the aperture may be embedded in a microfluidic circuit ensuring the transfer of the molecules of interest, e.g. DNA fragments, to the aperture.

In a preferred embodiment, the aforementioned circuit may be adapted to sense conductivity changes which occur when a molecule or different portions of a molecule pass through the aperture. Thus it is for example possible to achieve the sequencing of ss-DNA by detecting the occurrence of a tunneling current across the aperture (which should be/is base dependent).

To allow for a parallel processing of a plurality of single molecules, it is preferred that a plurality of apertures is provided. Preferably, these apertures are provided on/in a common carrier or substrate.

The invention further comprises an apparatus for the processing of single molecules, wherein said apparatus is obtainable by any of the methods described above. This means that the apparatus can be produced by (a) providing a "processing layer", (b) depositing a self-assembling resist on said processing layer and letting it self-assemble into a pattern of two phases, (c) removing selectively one phase of the self-assembling resist, and (d) generating at least one aperture in the processing layer through the mask of the remaining self-assembling resist. Other manufacturing methods for the apparatus comprise for example the generation of apertures by e-beam lithography.

According to a preferred embodiment, the aforementioned apparatus may comprise:

a) A bottom layer with a first aperture, for example a slit or preferably a hole. Said first aperture may have been produced by a method of the kind described above (i.e. by the application of a self-assembling resist) or any other method. The bottom layer may particularly be a non-conductive substrate.

b) An electrically conductive top layer that is disposed on said bottom layer and that has a second aperture which is disposed above the first aperture to commonly provide an aperture through which single molecules can pass, wherein the top layer is divided by the second aperture into two (electrically) disconnected parts. The top layer may for example consist of or comprise graphene, and/or the second aperture may be a slit. Moreover, the second aperture may have been produced by a method of the kind described above (i.e. by the application of a self-assembling resist) or any other method.

An advantage of the above apparatus is that it can be produced with some or all of the following features:

It may have a high number of apertures, for example more than 1000, preferably more than 10,000, most preferably more than 100,000.

It may have apertures that are arranged with a high spatial density, particularly a high linear density, for example of more than $3 \sim 10^5$ apertures per cm. With the approach of the present invention, apertures can be placed apart with a periodicity of <30 nm in a slit or trench in a way that allows for connecting all these apertures and measure the current over each aperture.

It may have apertures with a size (diameter) of less than 10 nm, preferably less than 7 nm, most preferably less than 5 nm.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components. Moreover, the right hand sides of FIGS. 13-24 and 26-38 all show a top view of the intermediate products, while the left hand sides of these Figures show a sectional view along the respective dashed line.

DETAILED DESCRIPTION OF EMBODIMENTS

The US 2010/0327847 A1 describes the use of a graphene layer/electrode in nanopore sequencing. It is proposed in this patent that a nanopore is embedded in the graphene, leaving areas besides the nanopore.

However, it is already known that graphene has a very high conductivity. A mobility of around 10,000 $cm^2/Vs$ at room temperature has been reported (K. S. Novoselov, A. K. Geim, S. V. Morozov, D. Jiang, Y. Zhang, S. V. Dubonos, I. V. Grigorieva, and A. A. Firsov, "Electric Field Effect in Atomically Thin Carbon Films", Science, 306 (204) 666-669). Hence, the current in the device of the US 2010/0327847 A1 will not or only hardly be modulated and the devices will have a poor effectiveness in determining the bases passing through the nanopore, as nearly all of the current will pass by the nanopore in the remaining graphene.

In view of this, it seems to be more effective to use nanogaps, as proposed by Postma (H. W. Ch. Postma, "Rapid sequencing of individual DNA molecules in graphene nanogaps", Nano Lett. 10 (2010) 420-425). As stated in this paper, using a nanogap has the additional advantage that problems of aligning the (nano)-electrodes to the nanopore are circumvented.

However, for practical purposes the device considered by Postma in his theoretical calculations has two important shortcomings:

To generate devices which can be easily manufactured the nanogaps or "slits" will have to have a finite length spanning the whole graphene electrode. This will be a dimension in the order of 0.1-1 μm. As single-stranded DNA (ss-DNA) to be measured is very flexible, this will allow DNA to pass through the nanogap in many ways, in particular folded. This will destroy the chance of measuring at the envisioned single-base resolution.

The graphene layers have no mechanical support and although graphene is a strong material the devices thus fabricated will not be very robust.

Shunt currents through the buffer liquid charged with ions will occur that may overwhelm any tunnel current to be measured.

To deal with these described issues, a crossed-slit (graphene) device can be used.

Figure 1:
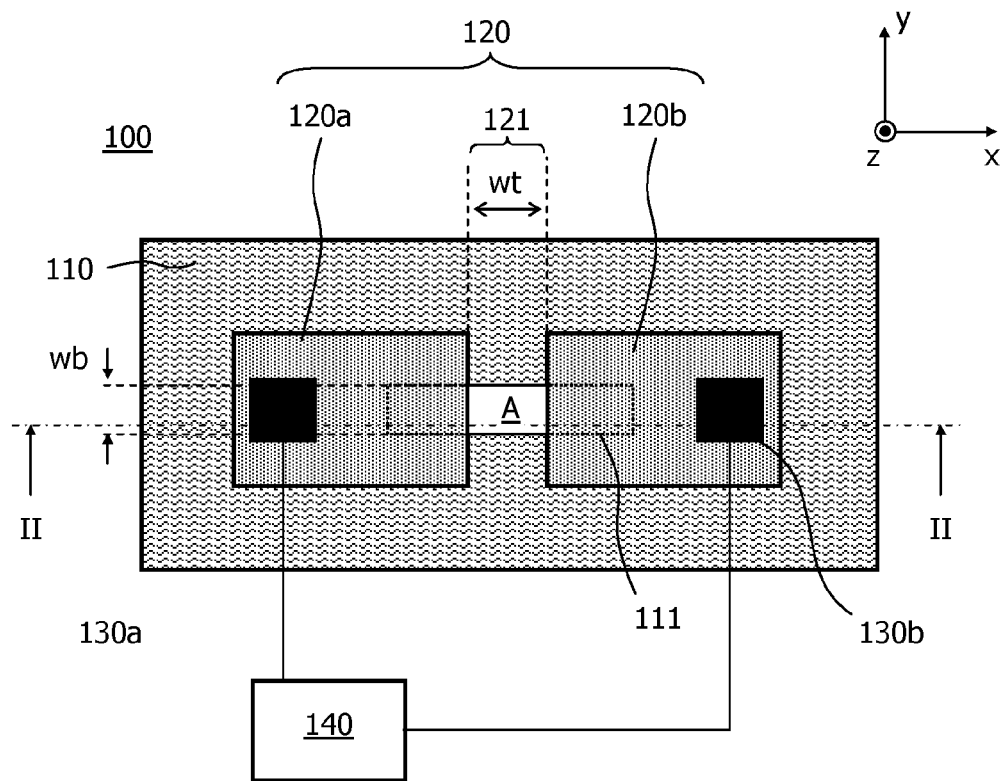
FIG. 1 shows a schematic top view onto a first apparatus according to the present invention.
Figure 2:
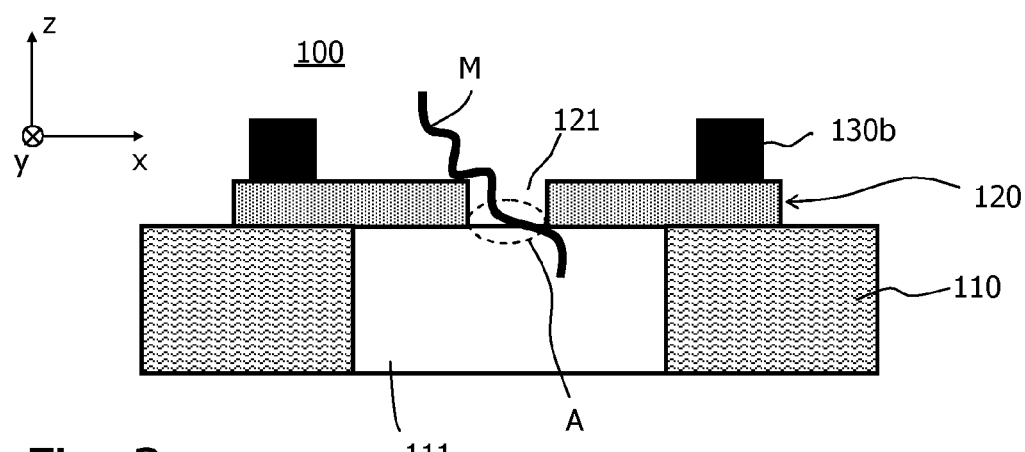
FIG. 2 shows a cross section through the apparatus of FIG. 1 along line II-II.

FIGS. 1 and 2 schematically sketch an exemplary apparatus 100 that is designed according to the aforementioned concept. The central components of this apparatus 100 are two layers, namely:

A "bottom layer" 110 comprising an elongated, rectangular first slit 111 of width wb that extends in x-direction.

A "top layer" 120 that is disposed on the aforementioned bottom layer 110, said top layer consisting of two disconnected parts 120*a*, 120*b* which are separated by a second slit 121 of width wt that extends in y-direction.

The first slit 111 and the second slit 121 are oriented perpendicular with respect to each other and overlap partially in a region of a (rectangular) aperture A through which single molecules M can pass.

As indicated in the Figures, the apparatus 100 further comprises contacts 130*a*, 130*b* disposed on the top layer parts 120*a*, 120*b*. Via these contacts, the top layer is connected to a circuit 140. This circuit 140 is adapted to sense electrical interactions that take place between the top layer parts 120*a* and 120*b* and single molecules passing through an aperture A.

It should be noted that the setup shown in FIGS. 1 and 2 is typically repeated periodically in x- and y-direction up to a wafer scale, yielding a high number of individually addressable apertures A.

Figure 3:
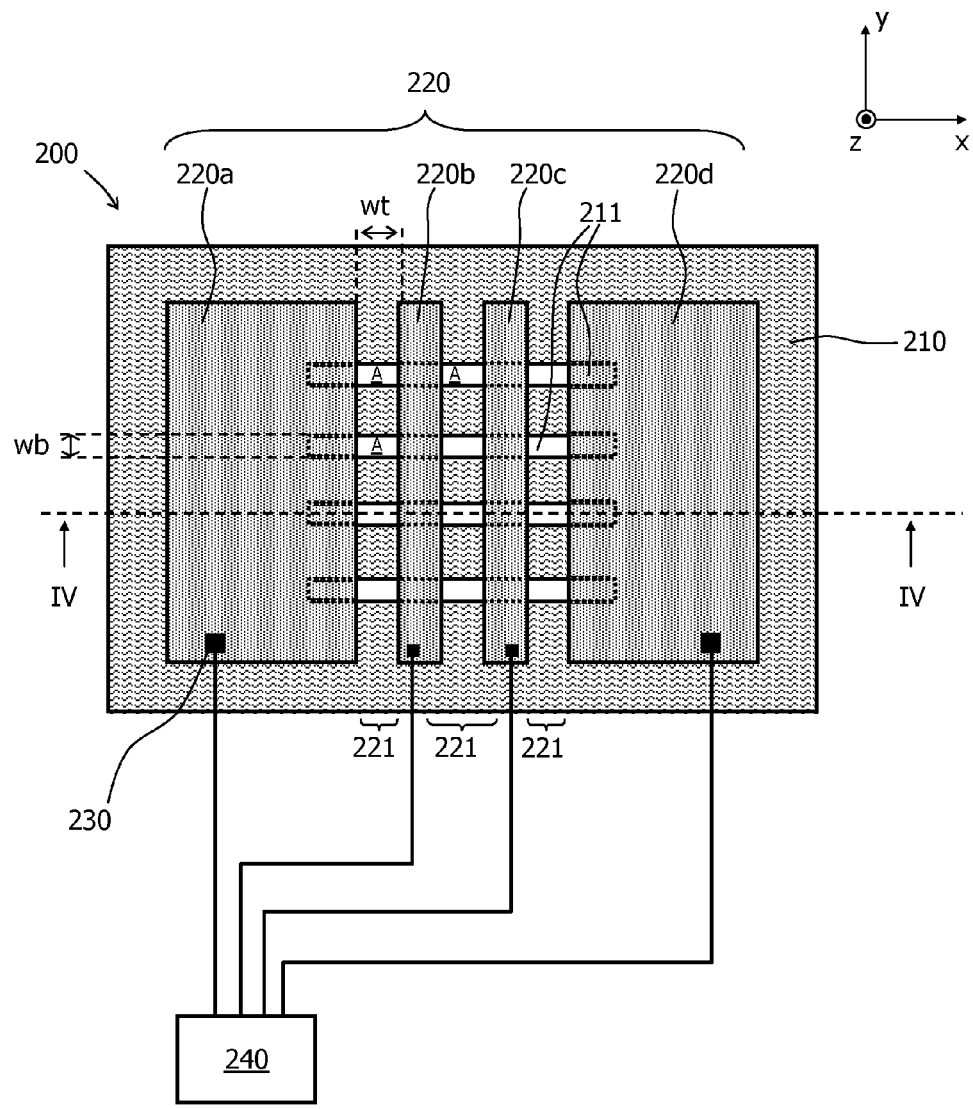
FIG. 3 shows a schematic top view onto a second apparatus according to the present invention in which several bottom-layer slits cross several top-layer slits.
Figure 4:
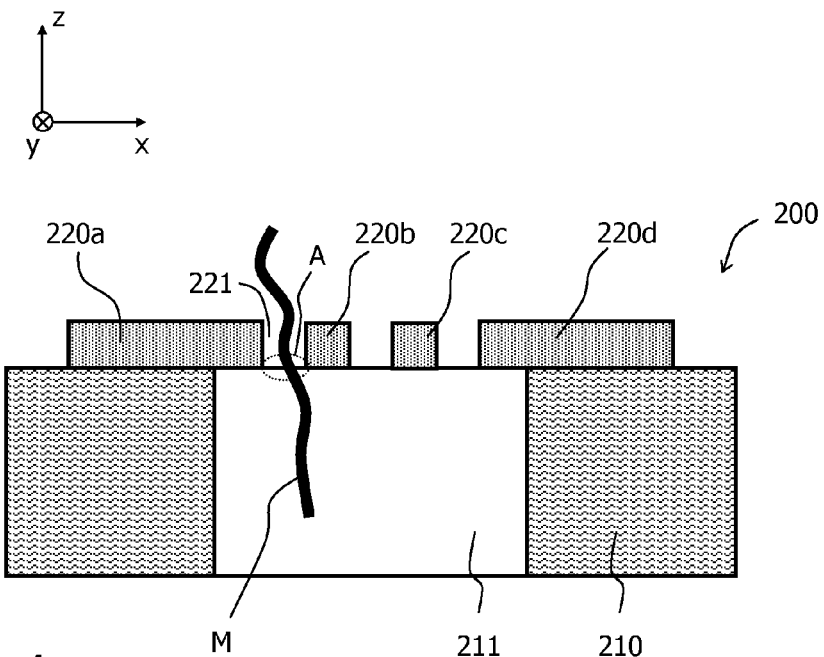
FIG. 4 shows a cross section through the apparatus of FIG. 3 along line IV-IV.

Moreover, FIGS. 3 and 4 show in similar views a second apparatus 200 that is designed analogously to the apparatus 100. The only difference is that several (here four) parallel slits 211 in the bottom layer 210 are crossed by several (here three) perpendicular slits 221 in the top layer 220. The various slits may have the same widths wt or wb, respectively, or different widths. If a molecule M passes through one of the apertures A that are generated in this way, an electrical signal is sensed via the adjacent parts 220*a*, 220*b* or 220*b*, 220*c* or 220*c*, 220*d* of the top layer 220.

The described crossed nano-slit devices 100, 200 have the following advantages over known devices to perform transverse-conductance based sequencing using graphene nanopores:

- Contrary to the nanohole device structure proposed in the US 2010/0327847 A1, a (tunneling) current will only be generated if and when DNA will pass through a nano-opening. Moreover the devices have the crucial advantage of doing measurement against zero background, i.e. a (very) limited to no signal occurs when no DNA passes through the device.
- This device structure can be manufactured easily and guarantee a single nano-opening through which ss-DNA can only pass. No nanohole has to be made, just two slits with nm width.
- The ss-DNA cannot pass through the devices in a folded manner, which would also preclude the detection of single bases.

An apparatus of the kind described above requires the generation of apertures or slits with a width (wt, wb) in the order of a few nm. A width of about 1-2 nm is for example required based on the calculations performed by Postma (above) of the tunneling current. Such slits might be generated by e-beam lithography, but this technology is not ideal for fast wafer scale manufacture of nanopore sequencing devices. Ideally, one would use an optical lithographic technique. However, optical techniques currently do not offer the 1-2 nm width required to make proper nano-slits.

In order to address this problem, it is proposed in an embodiment of the present invention to make the required apertures (slits, nanopores, etc.) in the described crossed-slit devices or other devices by using block co-polymer self-assembly. In particular, it is proposed to use block co-polymer self-assembly for graphene nanopore sequencing in three ways:

- Using block co-polymer self-assembly to reduce the narrow gaps made by e-beam or optical lithography (in a resist) even further to achieve the required nm dimensions (this approach has the advantage to be best compatible with the requirement of an electrical insulation over a nanogap in graphene).
- To reduce the size of nano-holes made by optical lithography (in a resist).
- The above, yet where the pre-patterns (in a resist) are made by e-beam.

Block copolymers have the ability to self-assemble into highly regular patterns with dense features at length scales down to about 5 nm (cf. Black et al., IBM J. Res. & Dev. 2007, 51(5), 605). The most commonly used block copolymers, diblock copolymers, are made of two blocks of polymerized monomers of different type, which are covalently linked together in a linear fashion. The block copolymer self-assembly process is driven by the minimization of free energy and is dependent upon the Flory-Huggins interactions parameter (measure for immiscibility of the different blocks). Block copolymers can form many different phases, mainly dependent upon the volume fractions of the blocks. When applied in thin films, in general only spherical, cylindrical and lamellar phases are observed in thin films. The self-assembly features can be aligned and directed by allowing the self-assembly to take place in between pre-patterned topographical features (grapho-epitaxy). Typical block copolymers to be used in relation to this invention comprise PS-b-PMMA (Poly(styrene-b-methyl-methacrylate)),
PS-b-PDMS (Poly(styrene-b-dimethylsiloxane),
PS-b-PEO (Poly(styrene-b-ethyleneoxide),
PS-b-PVP (Poly(styrene-b-vinylpyridine),
PMMA-b-PDMS (Poly(methylmethacrylate-b-dimethylsiloxane),
PS-b-PI (Poly(styrene-b-isoprene),
or other block copolymers that form self-assembled patterns.

Figure 5:
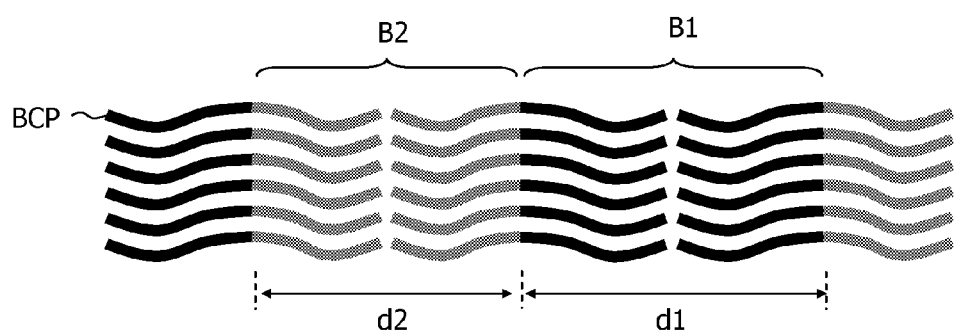
FIG. 5 schematically illustrates macromolecules of a self-assembling resist that assemble into a laminar pattern.

FIG. 5 schematically illustrates a laminar pattern formed by self-assemblage of block copolymer macromolecules BCP. The macromolecules BCP comprise an alternating sequence of blocks B1 and B2, wherein the first blocks B1 consist of a first type of monomer and the second blocks B2 consist of a different second type of monomer. The length of the different blocks B1, B2 (i.e. the number of contained monomers) may be the same or be different. The macromolecules BCP have at least approximately an identical spatial configuration which implies that they can self-assemble into a pattern in which equal blocks of different macromolecules BCP come close to each other. In the example shown, this results in a laminar pattern with stripes or "phases" of width d1 and d2, respectively. A pattern of this kind may for example be produced with block copolymers with volume fractions of 50% PS and 50% PMMA.

Figure 6:
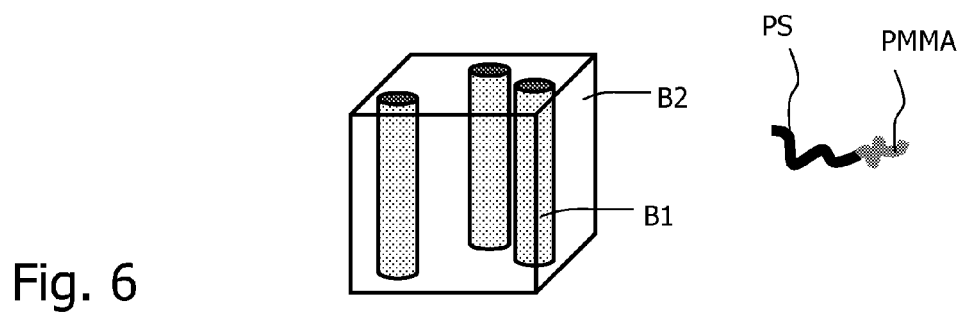
FIG. 6 schematically illustrates a self-assembling resist that assembles into a cylindrical pattern and one molecule of such a resist.

FIG. 6 illustrates another self-assembled pattern of a block copolymer, wherein said pattern comprises cylinders B1 of a first phase embedded in a second phase B2. A pattern of this kind may for example be produced with a block copolymer with volume fractions of 30% PMMA (as first phase B1) and 70% PS (as second phase B2).

FIGS. 7-12 show schematically consecutive basic steps of a manufacturing method according to the invention.

Figure 7:
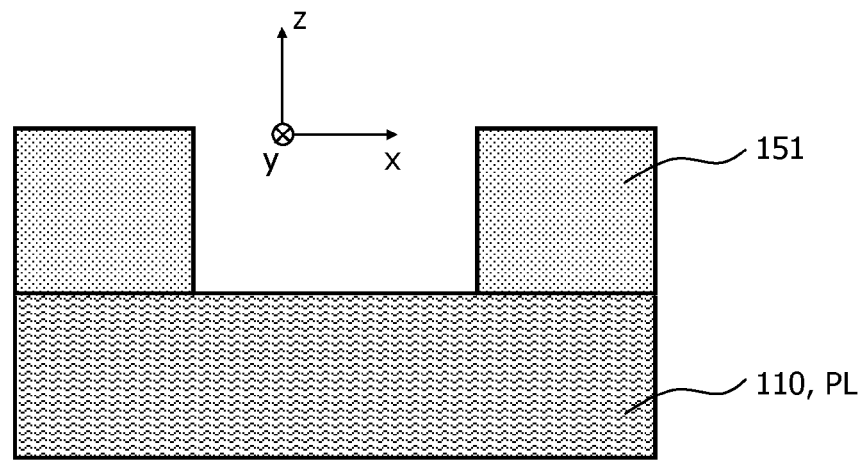
FIGS. 7-12 schematically illustrate consecutive basic steps of the generation of apertures in a processing layer with a single application of a self-assembling resist.

In FIG. 7, the manufacturing method starts with the provision of a "processing layer" 110 (or more generally referred to as "PL"), which can for example be the non-conductive substrate (e.g. $SiO_2$) of the apparatus 100 of FIGS. 1 and 2.

On one side of the processing layer 110, a "primary resist" 151 has been deposited and already been patterned, for example by optical lithography. This patterning results in walls of the primary resist 151 that confine a trench or channel between them.

Figure 8:
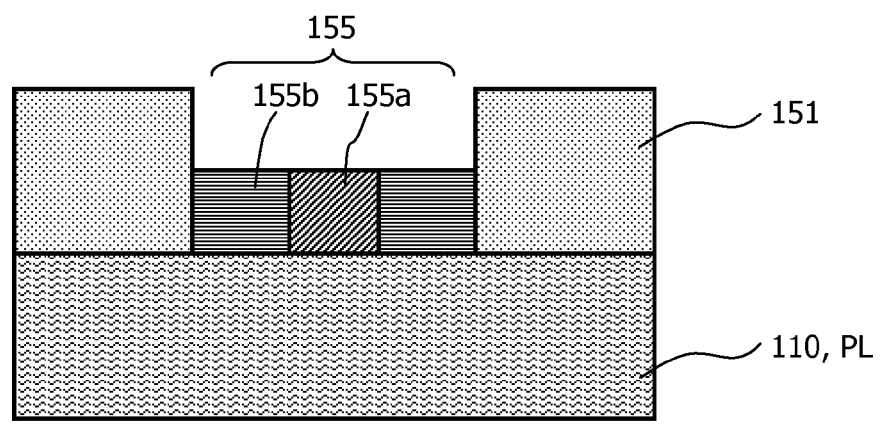

FIG. 8 shows the next step, in which a self-assembling resist 155 has been deposited in the aforementioned trench. According to the principles explained above, the self-assembling resist 155 has self-assembled into a pattern of a first phase 155a and a second phase 155b. In the shown example, the pattern is assumed to be a laminar pattern of three stripes extending in y-direction.

Figure 9:
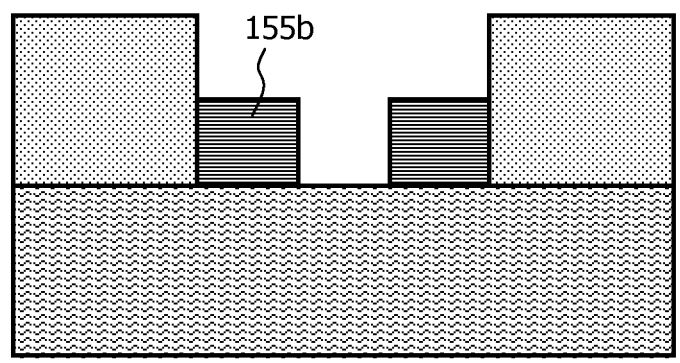

In FIG. 9, the central first phase 155a of the self-assembling resist has been removed, for example by selective etching, in which the etch resistance of the second phase 155b is significantly higher compared to that of the first phase 155a. Accordingly, only a pattern with parallel stripes of the second phase 155b remains.

In a different method, the first phase 155a can be removed selectively by photolytic degradation and subsequent dissolution of the degradation products. PMMA may for example degrade faster upon UV exposure (e.g. using 256 nm light) than PS. This method would be very suited since the whole wafer could be exposed to UV at once. Thus there is no need for using high resolution tools.

Figure 10:
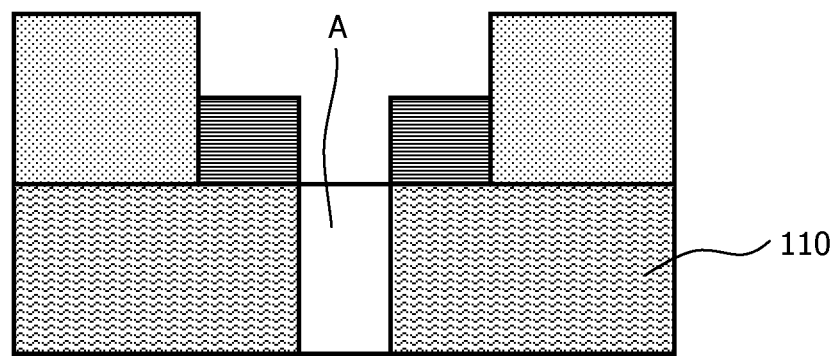

In FIG. 10, the aforementioned remainder of the second phase 155b has been used as a mask through which the processing layer 110 has been etched to generate an aperture A, which is a slit in this case. The slit A may later serve as aperture through which single molecules can pass. Alternatively the pattern formed by the aforementioned remainder of the second phase is transferred in an underlying hardmask layer (e.g. silicon oxide or silicon nitride) that is subsequently used to etch processing layer 110 to generate apertures A.

Figure 11:
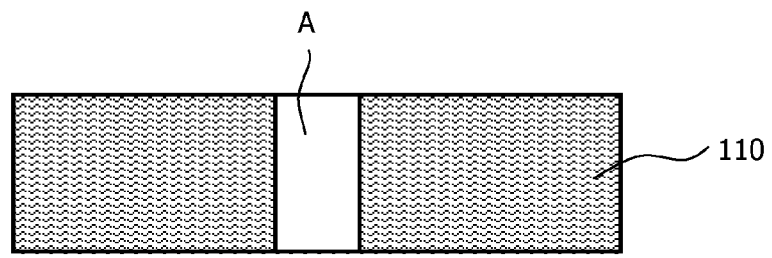

In FIG. 11, an (optional) additional step is shown in which the remainder 155b of the self-assembling resist and the primary resist 151 have been removed. Accordingly, only the processing layer 110 with the aperture A remains. It is however also possible to leave this step out, for example if the remaining resist on the processing layer is desired as an electrical insulation.

Figure 12:
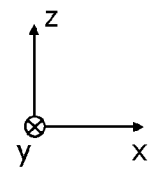
Figure 12:
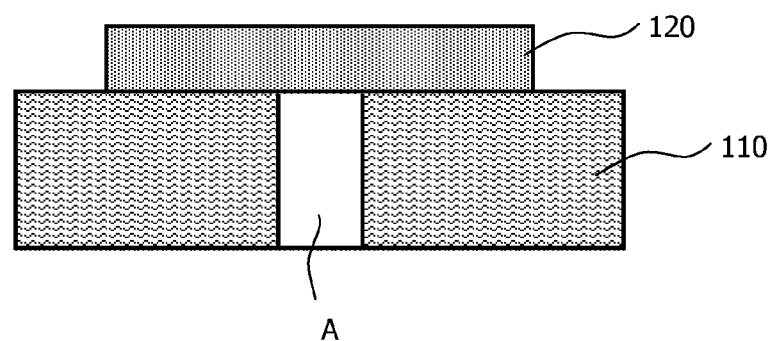

FIG. 12 shows the next step if the apparatus 100 of FIGS. 1 and 2 shall be produced. A top layer 120 (e.g. of graphene) is then deposited on the structured substrate 110. In this top layer 120, an aperture or slit in a direction perpendicular to the aperture A of the substrate 110 (i.e. in x-direction) is next produced with the very same method as shown in FIGS. 7-10, but now acting on the top layer 120 as "processing layer".

While FIGS. 7-11 show the practically important case in which there is just one central stripe 155a of a first phase of a self-assembling resist, it is in general also possible to use a plurality of more than three stripes of first and second phases and/or to use a pattern of cylinders in a matrix to produce several apertures (slits, holes) in parallel (cf. e.g. FIG. 15-17 or 22-24 below). An approach of this kind might for example be used to produce the apparatus 200 of FIGS. 3 and 4.

It should be noted that for each use of a biosensor apparatus, a disposable has to be made of millions of nanopores in parallel, to process the DNA for a single diagnostics test as the DNA of a single cell is comprised of $3\times10^9$ bases (if just a fraction of the genome shall be sequenced, fewer nanopores may suffice).

The described manufacturing procedure is advantageous as it allows using optical lithography. According to the state of the art of optical lithography in 2011, only features of about 22 nm size can be made by this technique. However, from a manufacturing standpoint using optical lithography would be ideal. It has two key advantages over e-beam lithography, namely that:

Whole wafers can be illuminated e.g. patterned at once, resulting in a much shorter time needed than with e-beam lithography, as in the latter case each line or pattern has to be written separately.

Potentially lower production costs as optical lithography is a conventional patterning technique (and self-assembly is intrinsically a low-cost process).

As current optical lithography does not have the means to form the nm size patterns needed, the above proposal solves this problem by using a block copolymer self assembly resists. This approach is for example ideal for forming the required nanogaps in an apparatus of the kind described above (FIGS. 1-4) as two perpendicular lines are required.

In experiments with a self-assembling resist, lines could be created with on average 9 nm line width, using a PS-b-PMMA block copolymer spun cast from a toluene solution. The sample was annealed for at 200° C. in an oven to facilitate the self-assembly of the block copolymers.

The aforementioned pattern could be used as an etch pattern to etch in the underlying dielectric layers such as $SiO_2$, $SiN_x$, or hexagonal boron nitride (h-BN, which closely matches to the graphene structure). Etching subsequently in a graphene layer is straightforward as a few seconds in an $O_2$-plasma is sufficient to etch a graphene single or double layer away.

Additionally or alternatively to the above described generation of slits, one may use the process to reduce the size of (round) nanopores formed by conventional optical lithography (cf. FIGS. 35-38 below). In experiments, the formation of 10-14 nm size nanoholes by block copolymer self-assembly could be observed inside 65 nm holes in a standard resist layer as obtained by conventional optical generation, using a different mix of block copolymers.

Although in the above description referred to the use of optical lithography, it is quite feasible to use e-beam lithography in the pre-patterning step. This would have the advantage over conventional e-beam lithography that much wider pattern can be made such that one could work under more favorable e-beam conditions. The required narrow gaps may then be made using block copolymer self-assembly.

FIGS. 13-24 illustrate another manufacturing procedure in which the basic steps described above (FIGS. 7-11) are repeated three times with different parameters and objects. The right hand sides of FIGS. 13-24 all show a top view of the intermediate products, while the left hand sides of these Figures show a sectional view along the respective dashed line.

Figure 13:
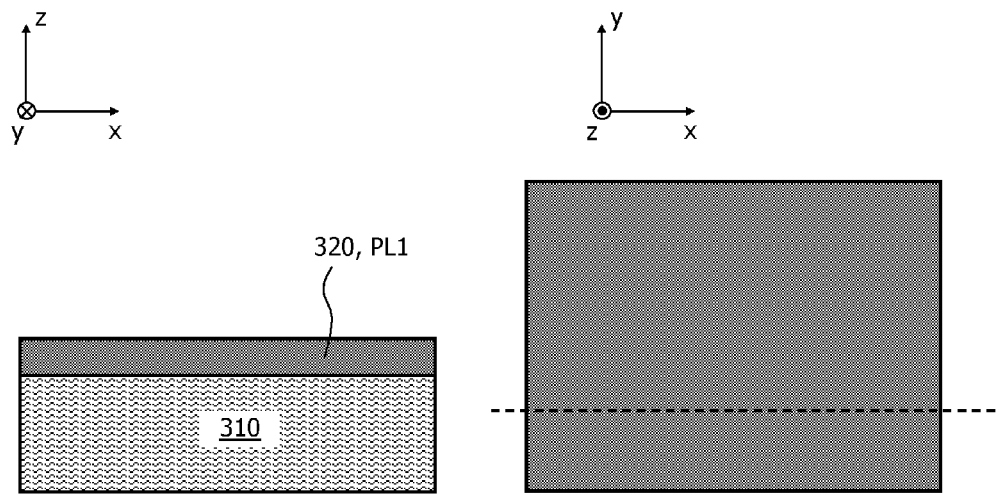
FIGS. 13-24 schematically illustrate consecutive steps of the manufacturing of an apparatus according to the invention comprising the generation of graphene stripes with the help of a self-assembling resist (FIG. 13-17), the perpendicular cutting of these graphene stripes with the help of a self-assembling resist (FIG. 18-21), and the generation of holes through the substrate as a final step with the help of a self-assembling resist (FIG. 22-24)

In FIG. 13, the procedure starts with the provision of a first processing layer 320 (or "PL1") that is disposed on a substrate 310. The substrate 310 may for example be a non-conductive material like $SiO_2$, while the first processing layer 320 is a conductive material, for example a graphene mono- or double-layer.

Figure 14:
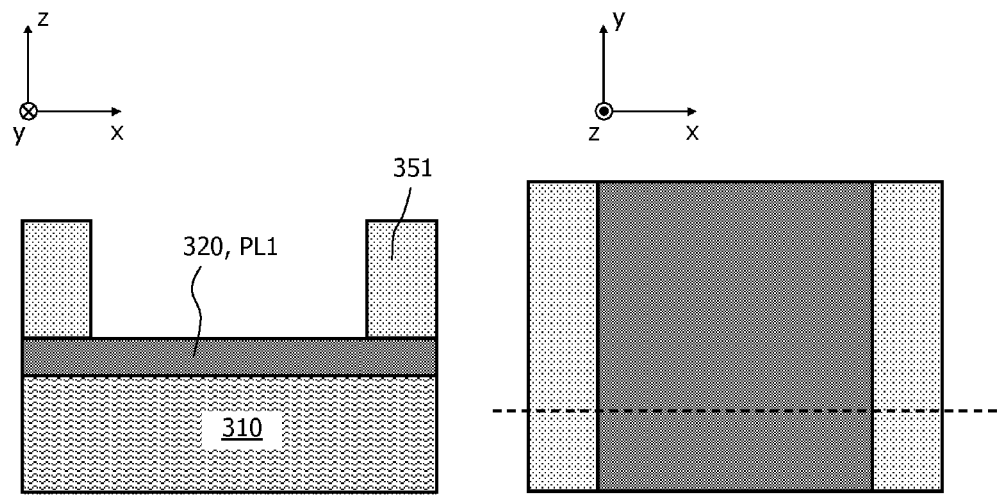

In FIG. 14, a (conventional) primary resist 351 has been deposited on the first processing layer 320 and already been patterned or structured, for example by optical lithography, to yield a (broad) trench in y-direction.

Figure 15:
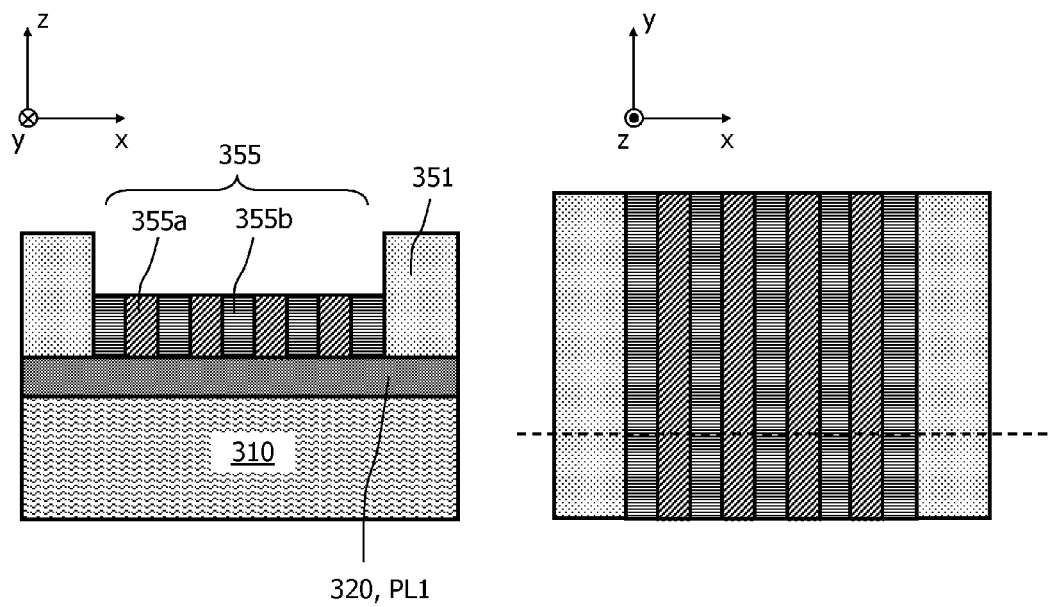

FIG. 15 shows that a self-assembling resist 355 has been deposited and has self-assembled into a laminar structure of alternating first phases 355a and second phases 355b in the trench of the primary resist.

Figure 16:
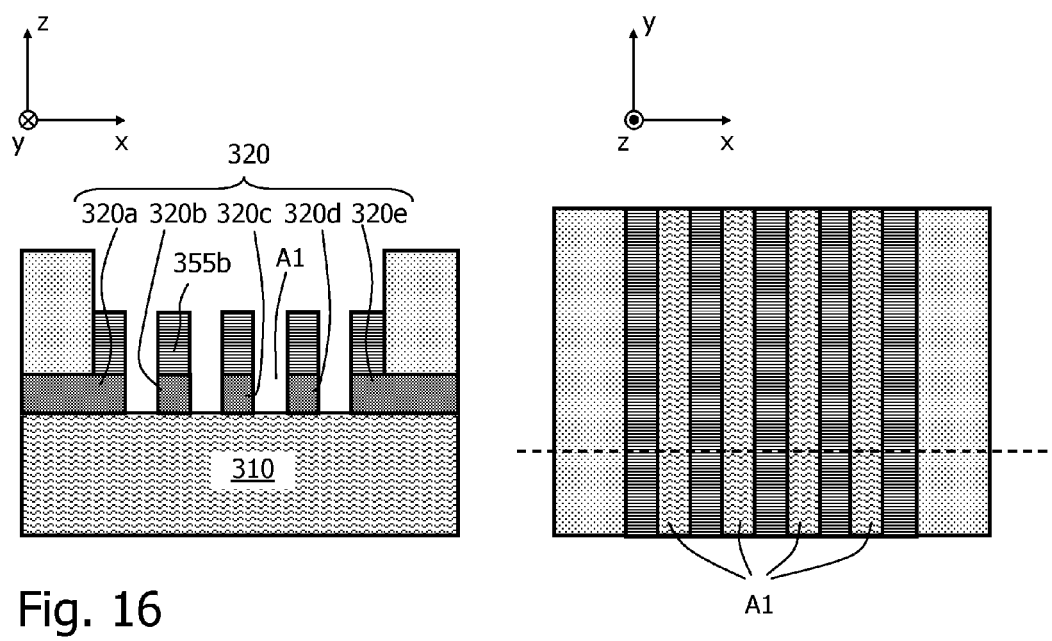

In FIG. 16, the first phases 355a of the self-assembling resist have been removed, leaving only the second phases 355b that serve as a mask for etching. Execution of this etching has generated the apertures A1 (slits) in the first processing layer 320. Accordingly, this layer is now divided into parallel stripes 320a, 320b, 320c, 320d, and 320e.

Figure 17:
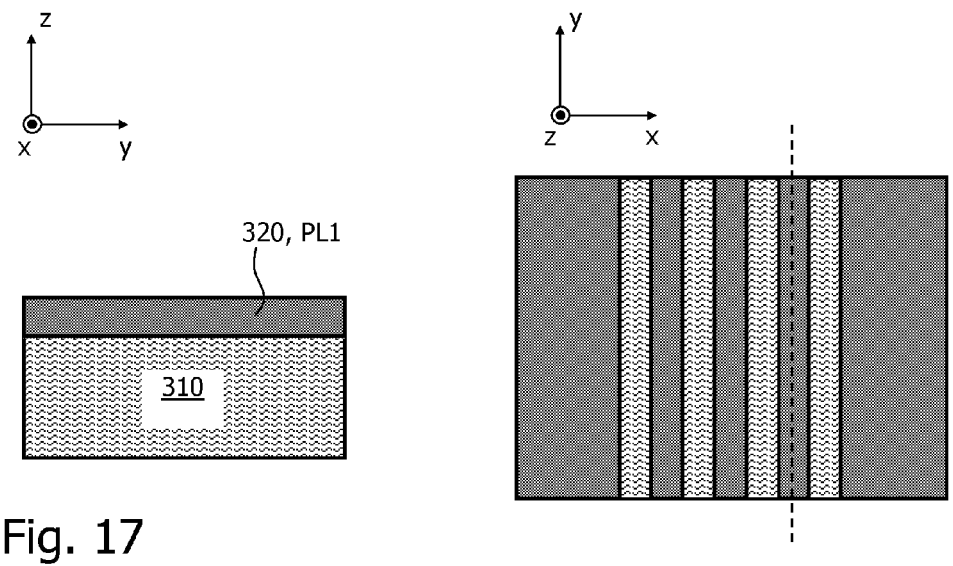

In FIG. 17, the primary resist 351 and the remainders 355b of the (first) self-assembling resist have been removed. Moreover, it should be noted that the sectional view on the left hand side is now rotated by 90° with respect to the sectional views in the previous Figures.

For the next processing steps, the (pre-patterned) graphene layer 320 will again be considered as the processing layer PL1 in which the next aperture will be generated, in this case a slit A2 perpendicular to the first slits A1.

Figure 18:
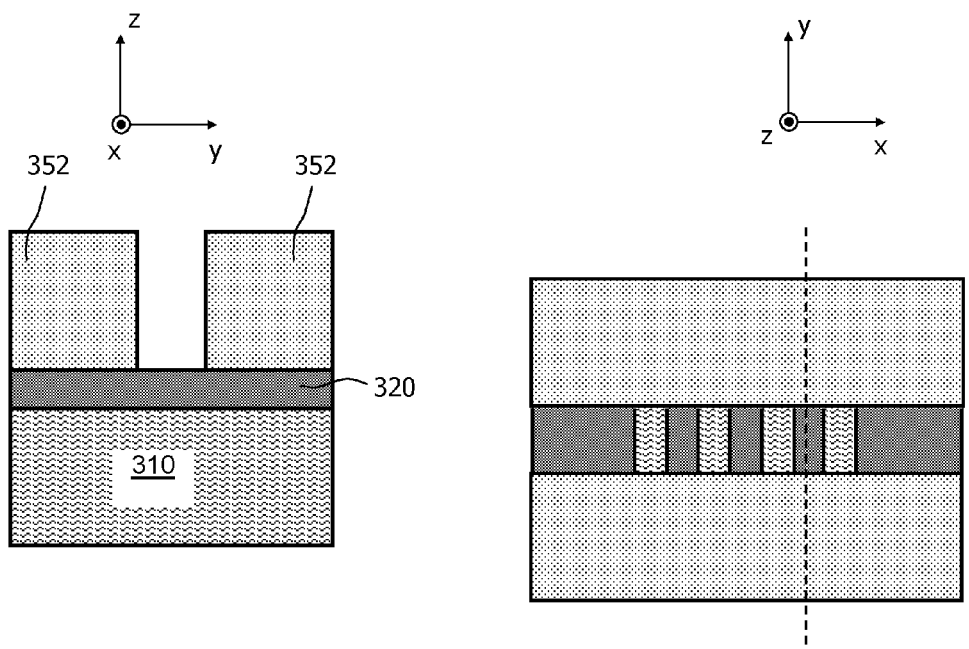

According to FIG. 18, a (second) primary resist 352 is deposited on top of the aforementioned processing layer PL1, wherein the resist as shown has already been patterned, for example by optical lithography, to yield a trench perpendicular to the prefabricated graphene stripes.

Figure 19:
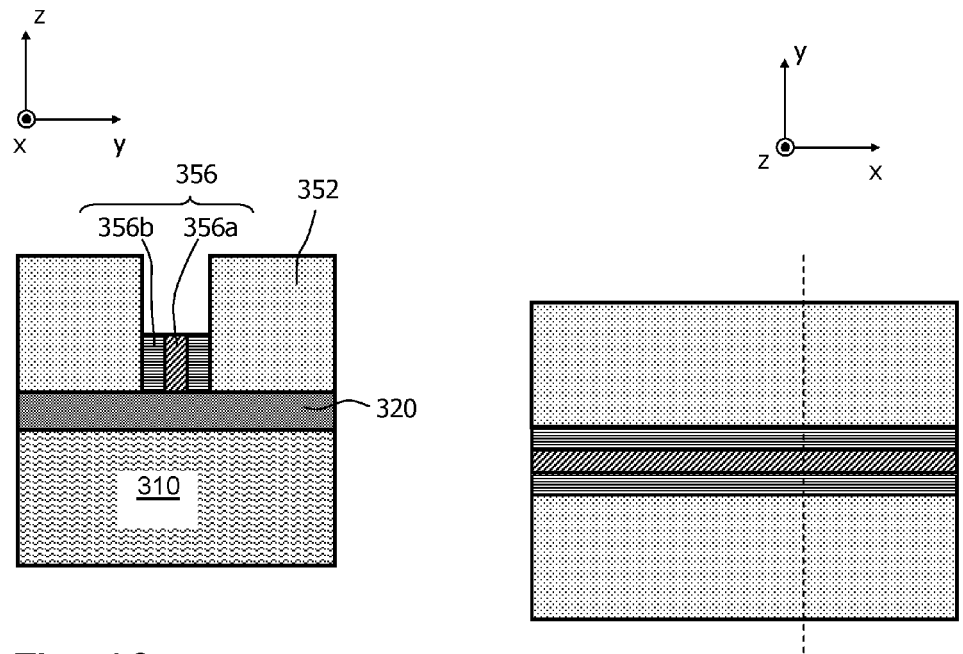

In FIG. 19, a (second) self-assembling resist 356 has been deposited in the aforementioned trench and self-assembled into a pattern of one central stripe of a first phase 356a embedded between two stripes of a second phase 356b.

Figure 20:
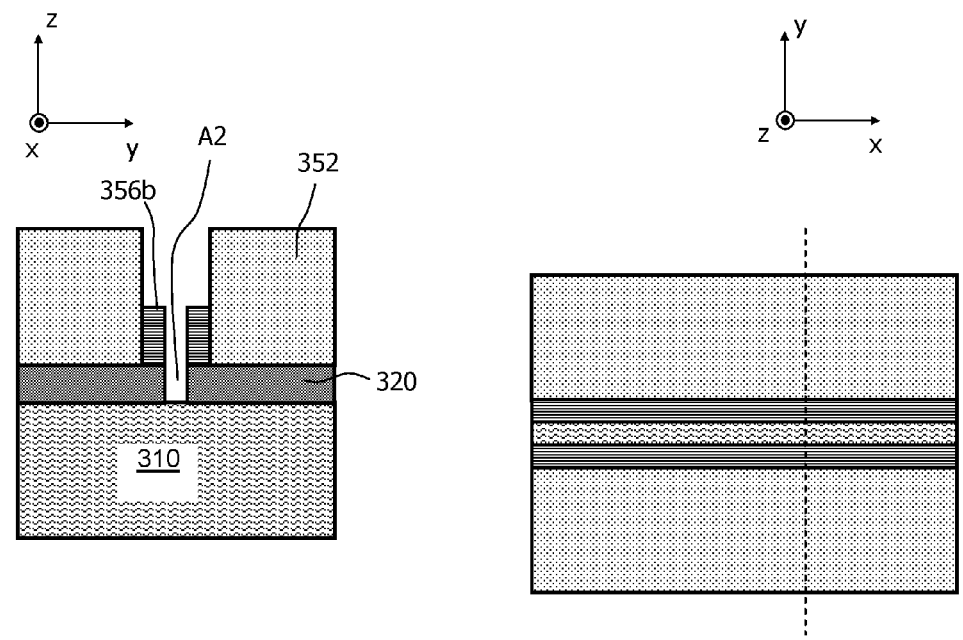

In FIG. 20, the first phase of the self-assembling resist has been removed and the remaining phase 356b of the resist has been used as a mask through which the processing layer 320 has been etched. This results in a narrow slit A2 in x-direction, cutting the prefabricated stripes of the processing layer in two.

For the next processing steps, the substrate 310 will be considered as the processing layer PL2 in which the next apertures will be generated, in this case holes A3 through the substrate 310.

Figure 21:
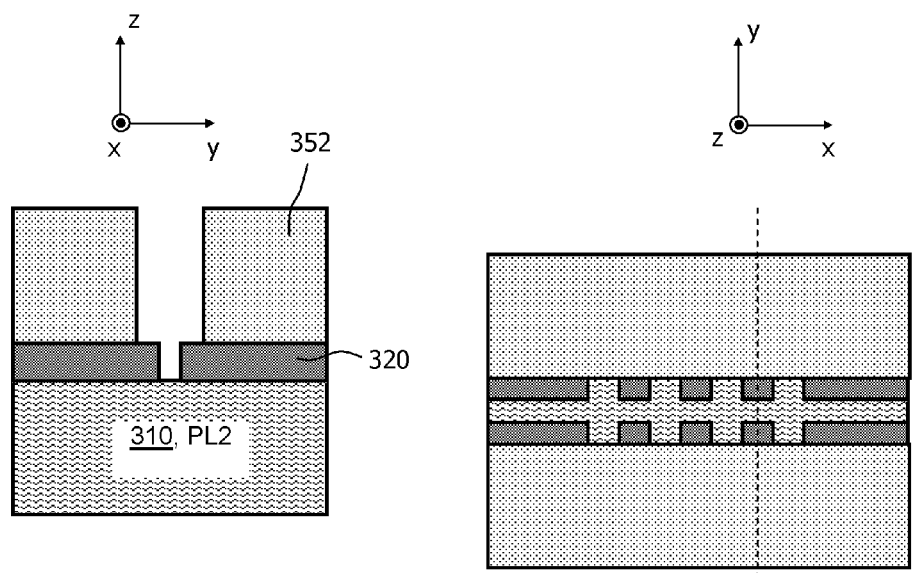

According to FIG. 21, this sub-procedure starts with the removal of the remainder 356b of the previous self-assembling resist, leaving behind the primary resist 352 with its central trench in x-direction.

Figure 22:
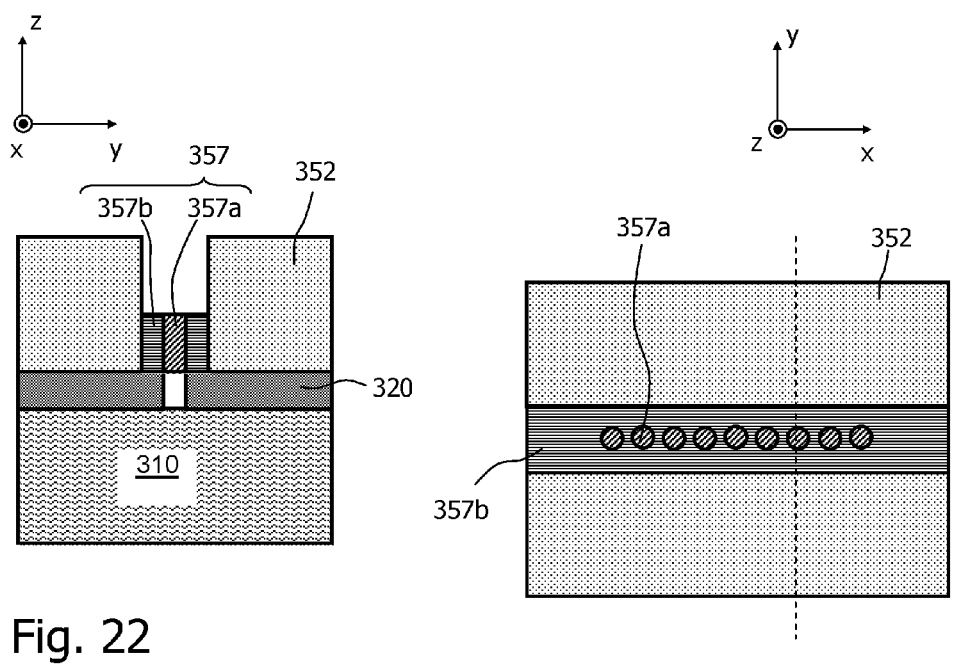

FIG. 22 shows that a (third) self-assembling resist 357 has been deposited and self-assembled into a pattern of cylinders 357a of a first phase embedded in a second phase 357b.

Figure 23:
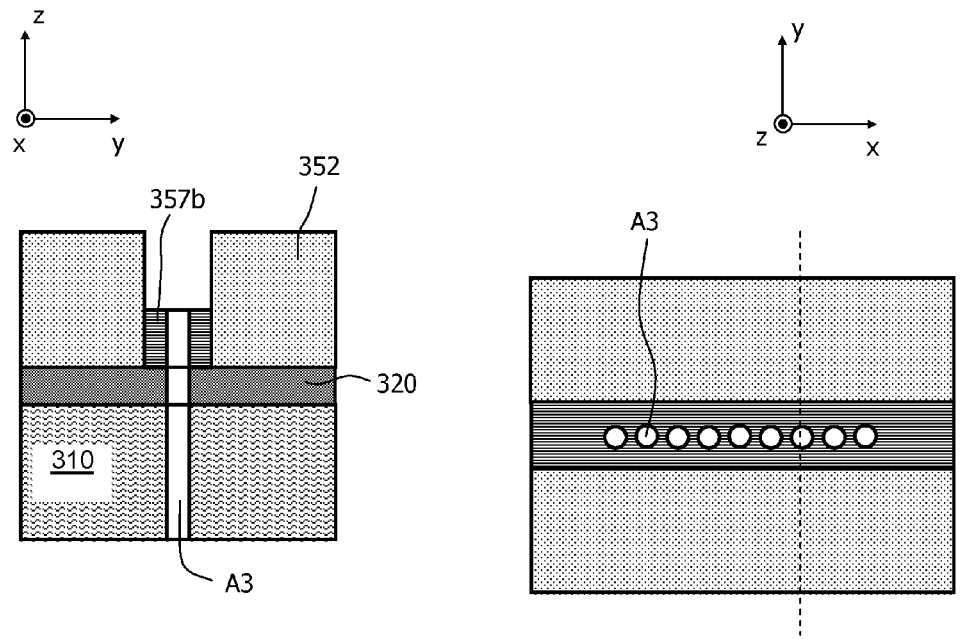

In FIG. 23, the first phase of the self-assembling resist has been removed and the remaining phase 357b of the resist has been used as a mask through which the substrate 310 (second processing layer) has been etched. This results in a row of circular apertures or holes A3 that reach through the substrate 310.

Figure 24:
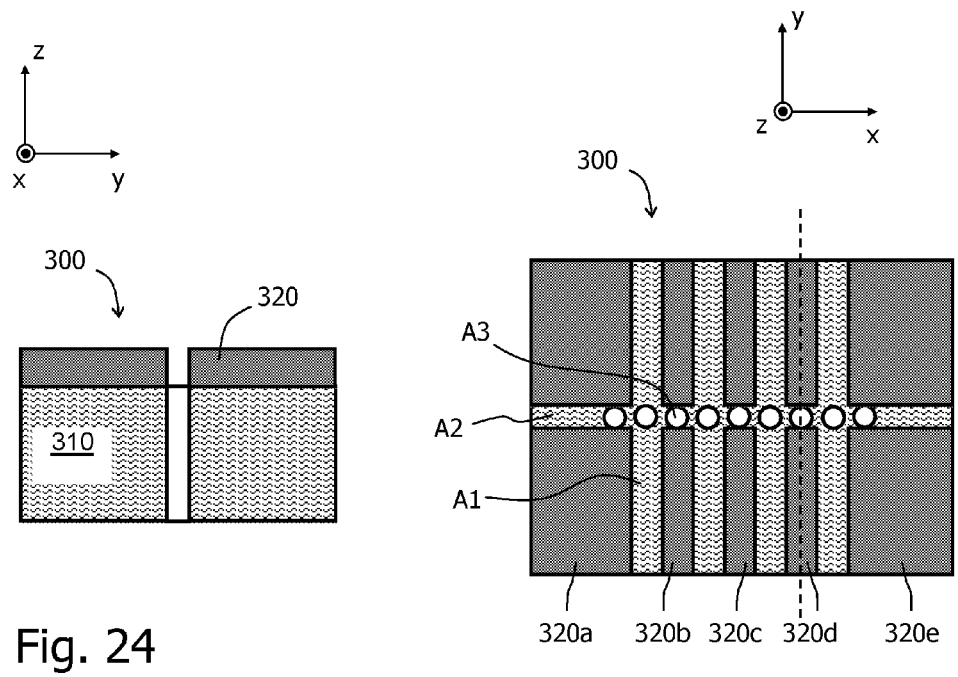

FIG. 24 shows the final device 300 after the (optional) removal of the (second) primary resist 352 and the remaining (third) self-assembling resist 357b. The device may be subject to further manufacturing steps, for example the application of additional (e.g. insulating) layers and/or the connection to a circuit (cf. FIGS. 1-4).

Figure 25:
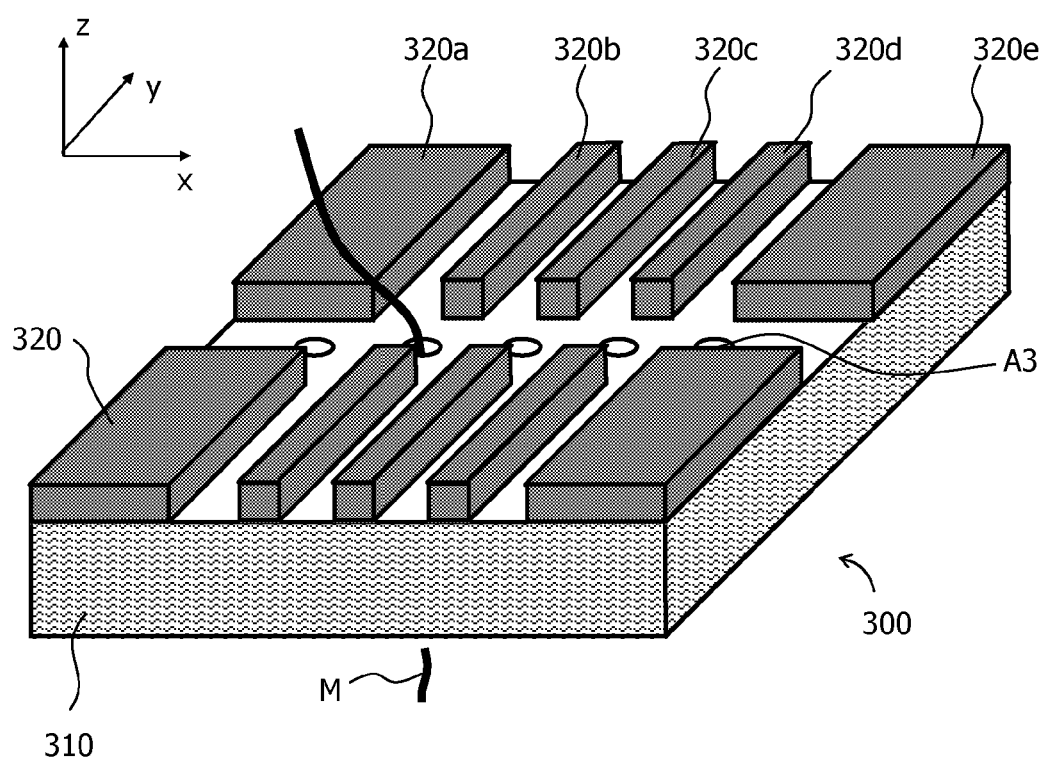
FIG. 25 shows schematically a perspective view of the apparatus generated by the procedure shown in FIGS. 13-24.

FIG. 25 shows a schematic perspective view of the apparatus 300 (dimensions are not to scale). It can be seen that parallel lines or bars 320a-320e of conductive graphene remain on the substrate 310. Each of these lines is cut into two pieces that may be connected to a circuit (not shown) and that lie on opposite sides of a (nano-) hole or aperture A3 through which single molecules M can pass. Moreover, each of the resulting electrode pairs 320a-320e may be put in its own microfluidic circuit (not shown).

FIGS. 26-29 schematically illustrate a modification of the manufacturing procedure described above with respect to FIGS. 13-24. In this approach, the holes A3 through the substrate 310 are generated with the help of a self-assembling resist as the first step, not as the last.

Figure 26:
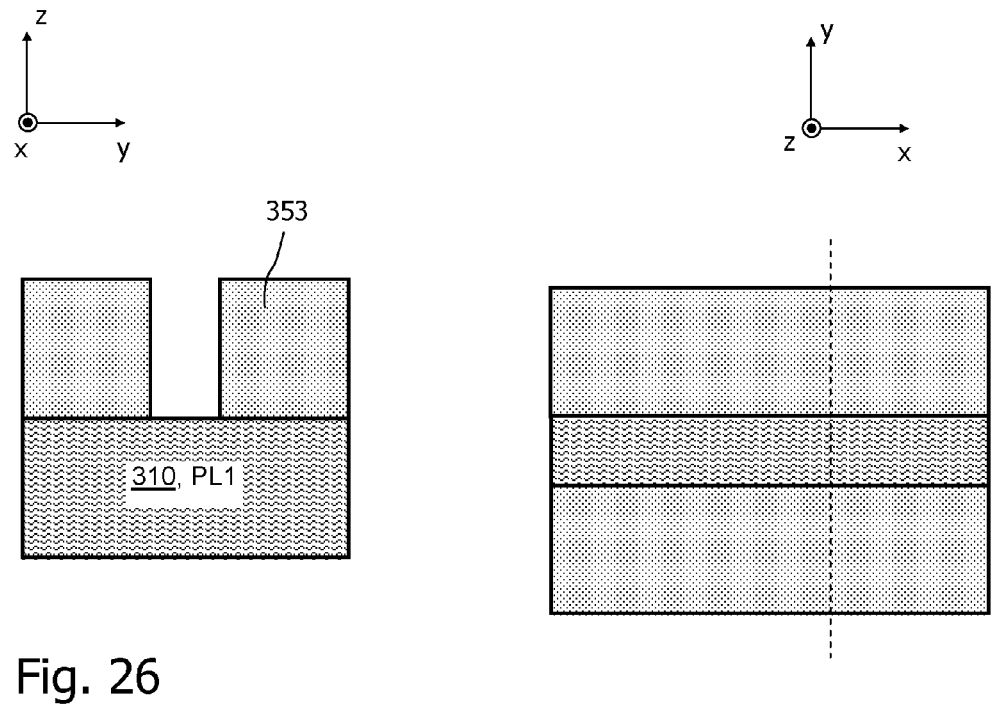
FIGS. 26-29 schematically illustrate a modification of the manufacturing procedure of FIGS. 13-24, wherein the generation of holes through the substrate with the help of a self-assembling resist is a first step.

According to FIG. 26, the procedure starts with the deposition of a primary resist 353 onto the substrate 310 (without graphene on top), which is considered as the processing layer PL1 for the next steps. Moreover, the primary resist 353 has been patterned, e.g. by optical lithography, yielding a central trench in x-direction.

Figure 27:
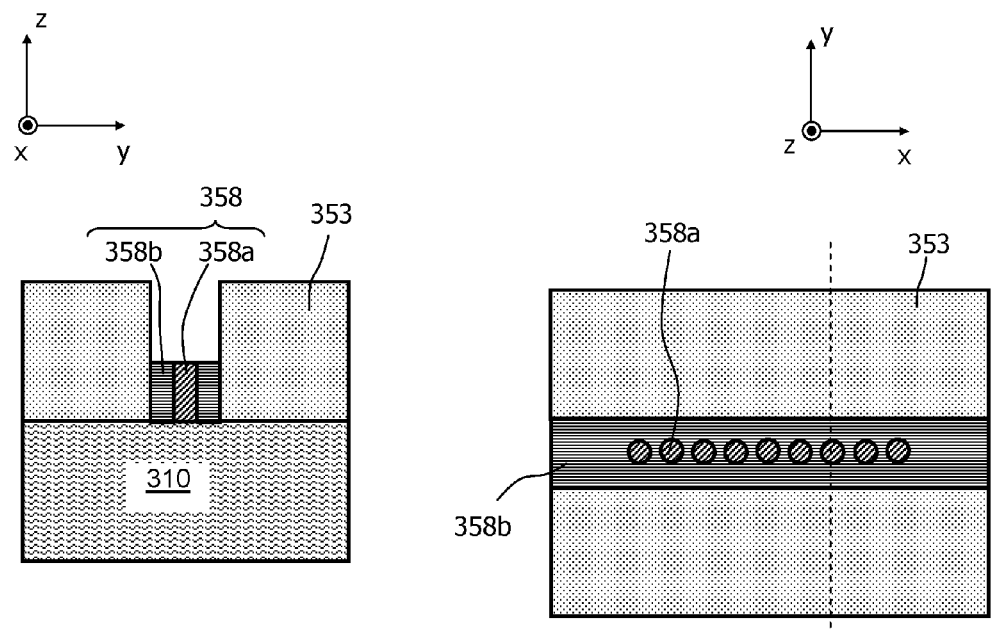

FIG. 27 shows that a self-assembling resist 358 has been deposited and self-assembled into a pattern of cylinders 358a of a first phase embedded in a second phase 358b.

Figure 28:
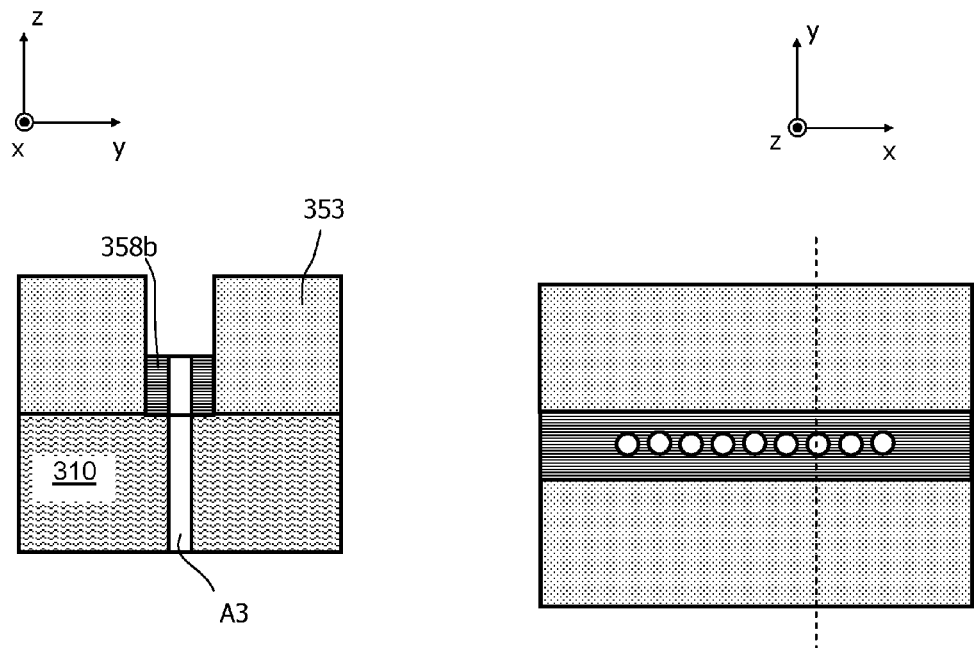

In FIG. 28, the first phase of the self-assembling resist has been removed and the remaining phase 358b of the resist has been used as a mask through which the substrate 310 (processing layer) has been etched. This results in a row of circular apertures or holes A3 that reach through the substrate 310.

Figure 29:
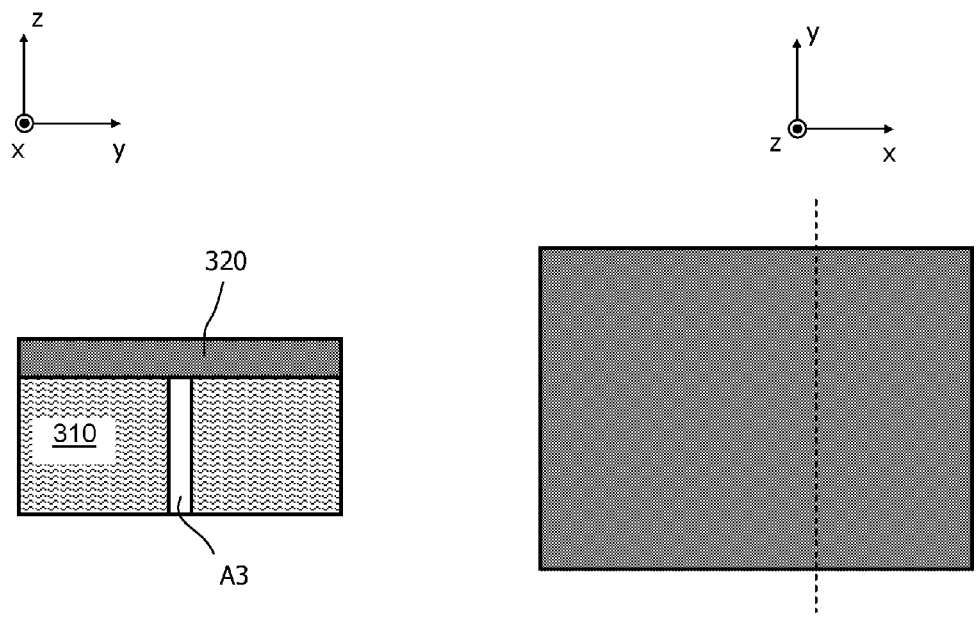

FIG. 29 shows the device after a graphene layer 320 has been deposited on top of the substrate 310, covering the holes A3. The further manufacturing can now continue analogously to the steps of FIGS. 13-21, according to which parallel stripes are first produced in the graphene layer (by slits A1) which are then cut perpendicularly in two (by a slit A2). In contrast to FIG. 21 above, the holes or apertures A3 in the substrate 310 are now already present, allowing to jump directly to the accomplished apparatus 300 of FIG. 24.

FIGS. 30-38 schematically illustrate consecutive steps of an alternative manufacturing procedure of an apparatus 400.

Figure 30:
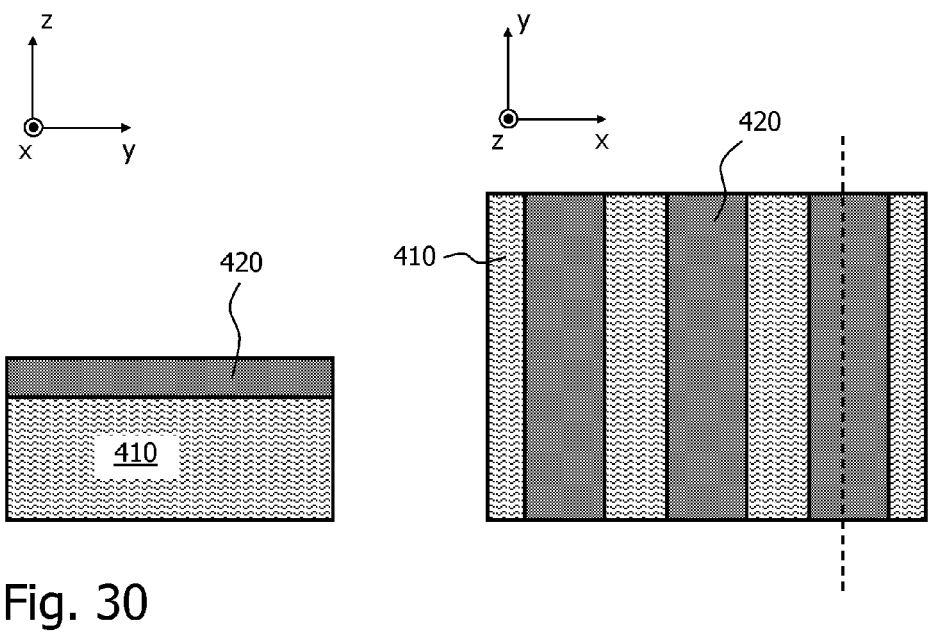
FIGS. 30-38 schematically illustrate consecutive steps of the manufacturing of an apparatus according to the invention comprising the generation of graphene stripes with optical lithography (FIG. 30), the perpendicular cutting of these graphene stripes with the help of a self-assembling resist (FIG. 31-34), and the generation of holes through the substrate as a final step with the help of a self-assembling resist (FIG. 32-38).

This procedure starts in FIG. 30 with the generation of (broad) stripes in a graphene layer 420 with the help of e.g. optical lithography. This graphene layer 420 is the "processing layer" PL1 for the next steps.

Figure 31:
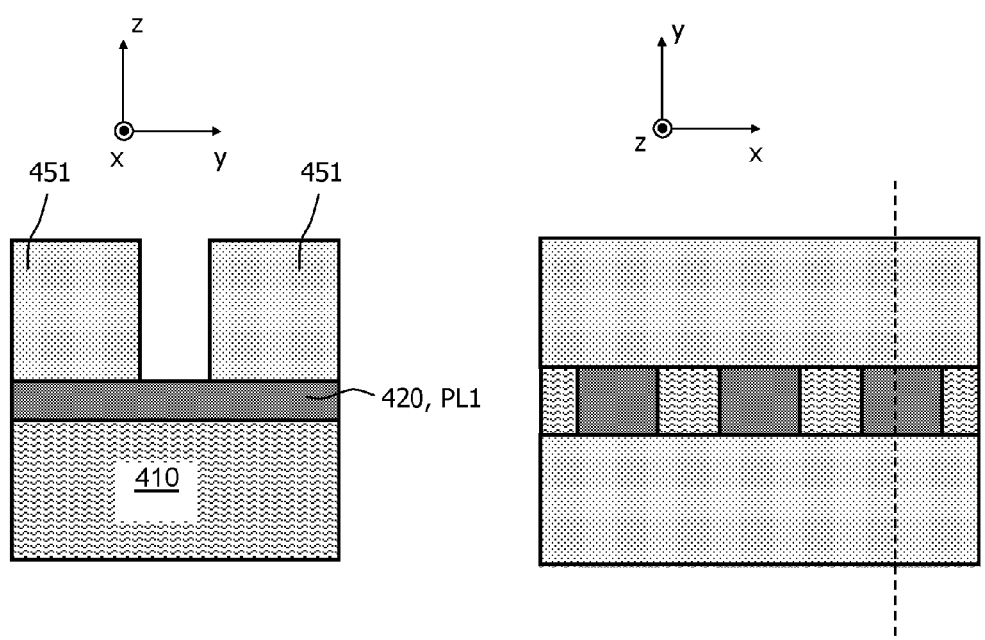

According to FIG. 31, a primary resist 451 has been deposited on the graphene layer 420 and already been patterned, for example by optical lithography, to yield a central trench perpendicular to the graphene stripes.

Figure 32:
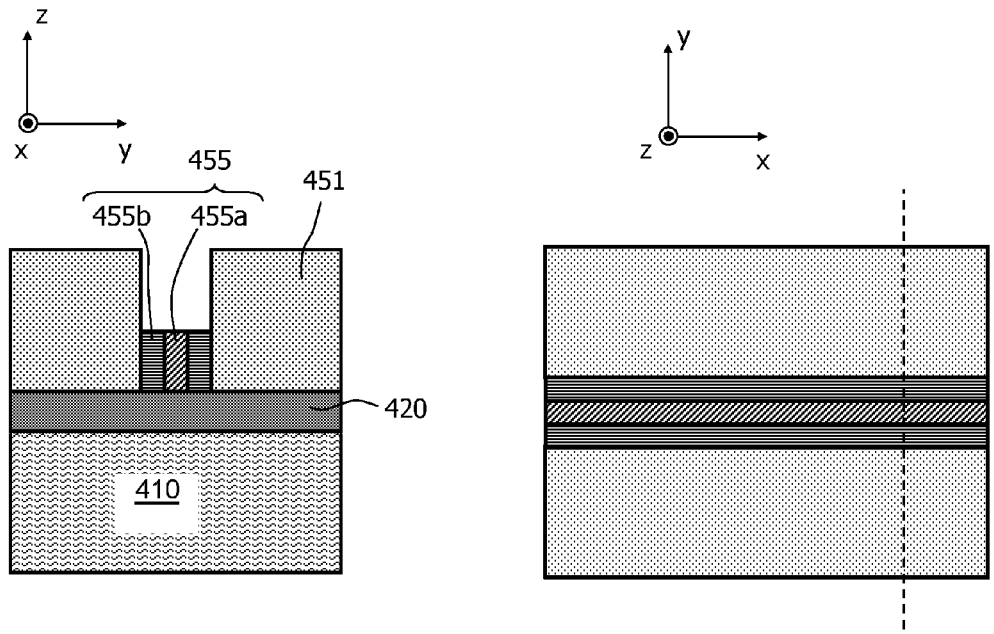

FIG. 32 shows the next step, in which a self-assembling resist 455 has been deposited in the aforementioned trench and has self-assembled into a pattern of three stripes of a first phase 455a and a second phase 455b extending in x-direction.

Figure 33:
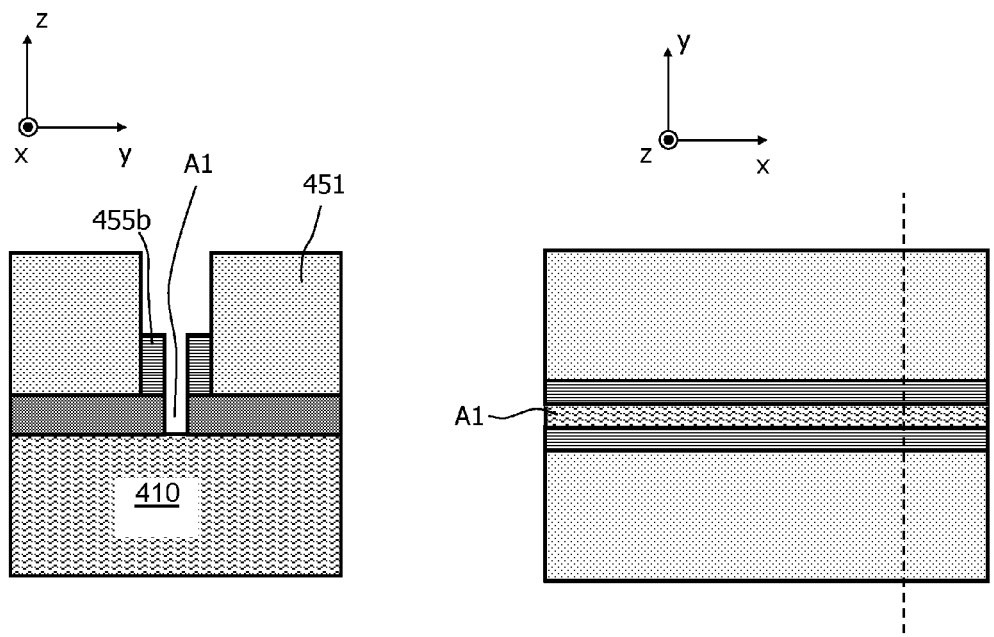

In FIG. 33, the central first phase of the self-assembling resist has been removed, and the remainder of the second phase 455b has been used as a mask through which the processing layer 420 has been etched to generate a slit or aperture A1.

Figure 34:
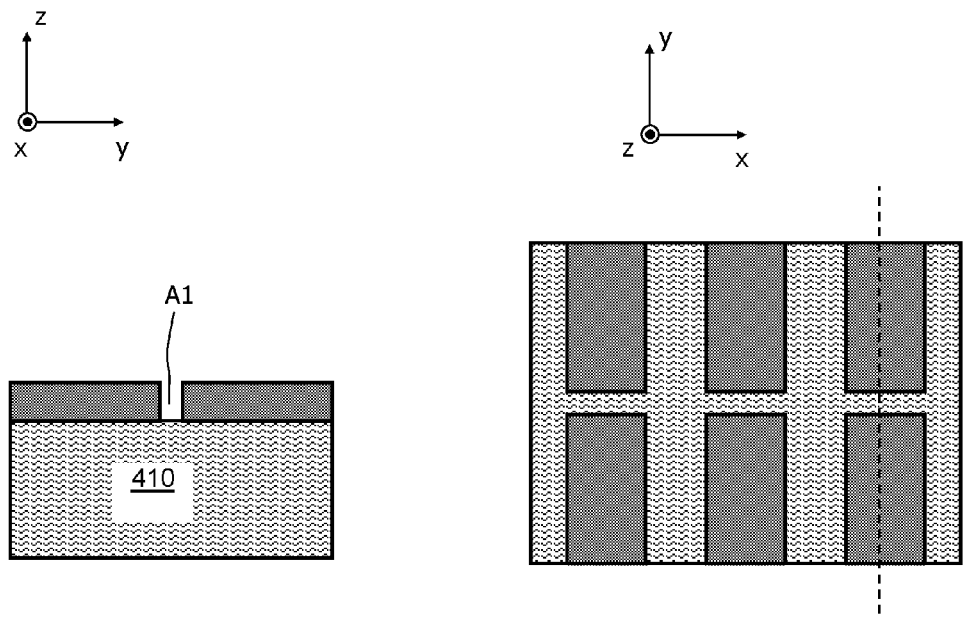
Figure 35:
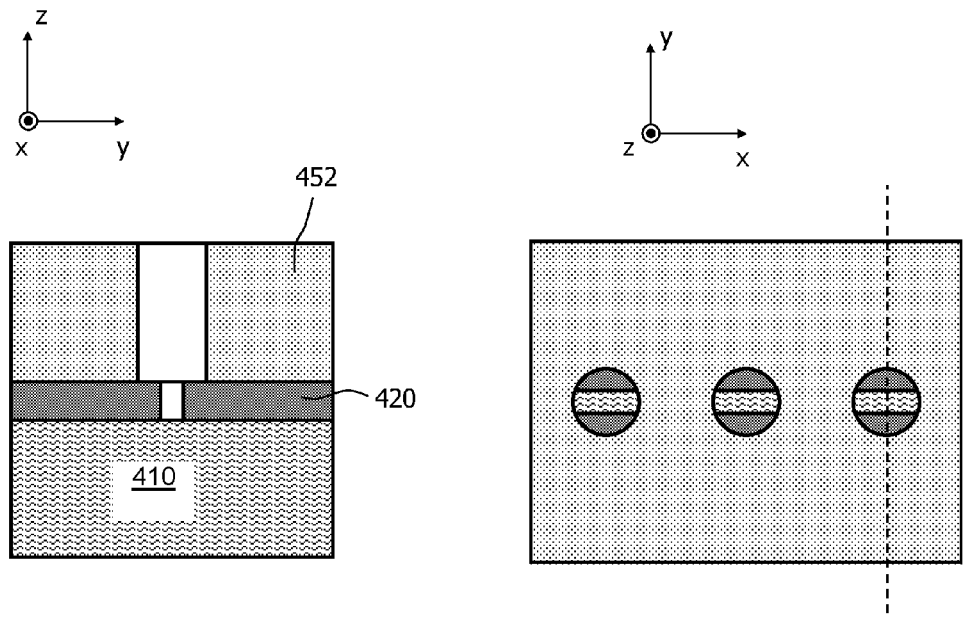

According to FIG. 34, the remainder 455b of the self-assembling resist and the primary resist 451 have been removed. This finishes the sub-process of cutting the graphene stripes perpendicularly in two.

Next, holes through the substrate 410 have to be generated. This starts in FIG. 35 with the deposition of a further primary resist 452 on the pre-patterned graphene layer 420. Moreover, this primary resist 452 is patterned to yield a row of holes.

When optical lithography is used for the aforementioned purpose, it is possible to process a whole wafer (of which the Figures show only a tiny fraction) in parallel. However, these holes are comparatively large and hence need to be narrowed for e.g. the intended application of nanopore sequencing.

Figure 36:
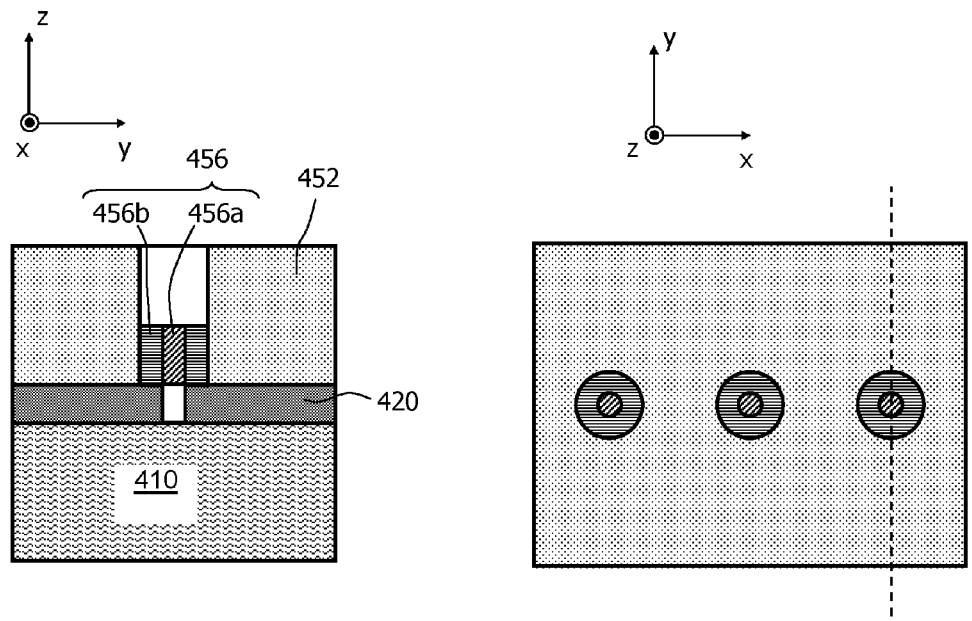

This narrowing starts in FIG. 36 with the deposition of a self-assembling resist 456 in the prefabricated holes, wherein this resist self-assembles into a pattern of cylinders 456a of a first phase surrounded by a second phase 456b.

Figure 37:
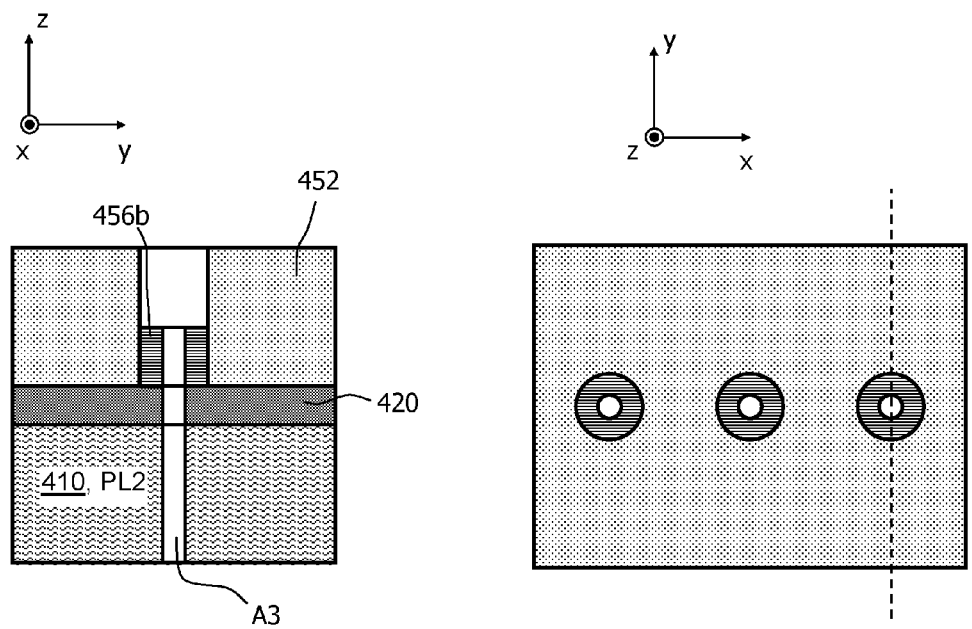

In FIG. 37, the first phase of the self-assembling resist has been removed and the remaining phase 456b of the resist has been used as a mask through which the substrate 410 (second processing layer PL2) has been etched. This results in a row of small circular apertures or holes A3 that reach through the substrate 410.

Figure 38:
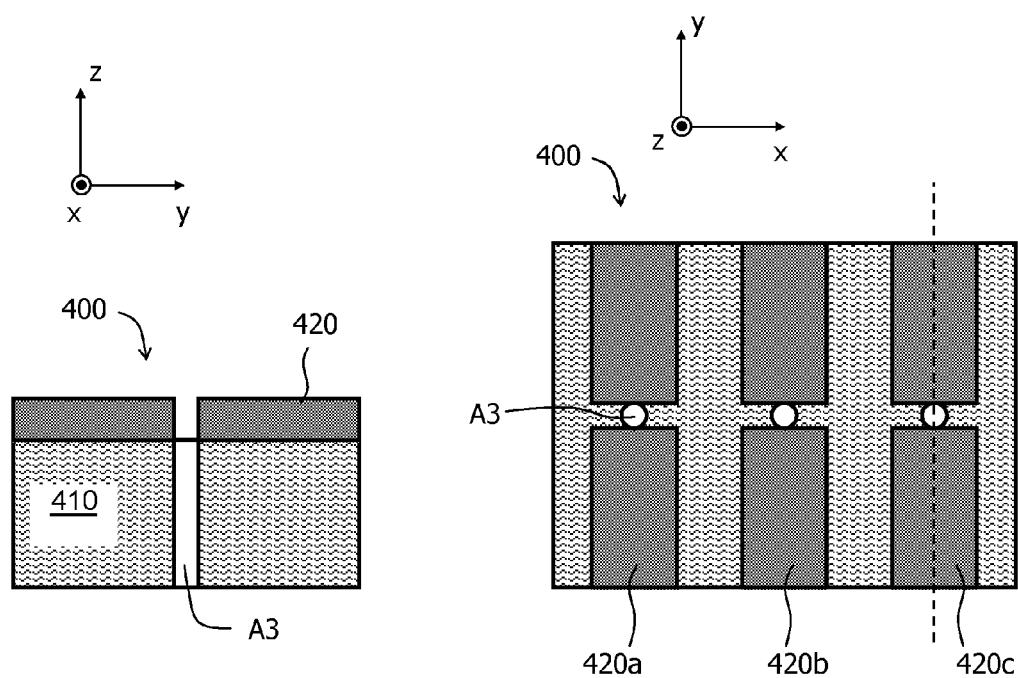

FIG. 38 shows the final apparatus 400 after the (optional) removal of the primary resist 452 and the remaining self-assembling resist 456b. The apparatus 400 has parallel lines or bars 420a-420c of conductive graphene, wherein each of these lines is cut into two pieces that may be connected to a circuit (not shown) and that lie on opposite sides of a (nano-) hole or aperture A3 through which single molecules M can pass. The device may be subject to further manufacturing steps, for example the application of additional (e.g. insulating) layers and/or the connection to a circuit (cf. FIGS. 1-4). Moreover, it is preferred that each of the electrode pairs 420*l*-420*c* is put in its own microfluidic circuit.

A procedure of the kind described above has been executed in an experiment. A silicon substrate was locally etched on the backside to a thickness of 100 nm or below. The substrate was provided with a graphene monolayer or bilayer. A resist was spincoated on the graphene layer and a trench of 100-300 nm was created in the resist layer. The trench was filled with a symmetrical block copolymer that formed a lamellar pattern upon annealing. The graphene layer may optionally be pre-treated with a neutral orientation layer, to achieve perpendicular alignment of the block copolymers. The lamellar block copolymer pattern was used as an etch resist mask to transfer the line spacer pattern in the graphene layer. Thereafter the remaining block copolymer and resist was stripped from the substrate and a new resist layer was applied. A new trench with a trench width of approx. 30-60 nm was created by optical lithography perpendicular to the first trench. This trench was filled with an asymmetric block copolymer, capable of forming a cylindrical phase with perpendicular orientation of the cylinders with respect to the substrate and the cylinders being located on top of the thin graphene lines. The graphene layer may optionally be pre-treated with a neutral orientation layer, to achieve perpendicular alignment of the block copolymers (brush polymers may for example be used for this purpose, especially random brush copolymers consisting of randomly polymerized monomers A and B with an end group that can be reacted to surfaces). Again the block copolymer layer was used as an etch mask to etch through the graphene and through the underlying substrate. After stripping of the remaining block copolymer, an array of nanopores with thin graphene electrodes was obtained. Subsequently, the required contacts and the rest of the device could be made by conventional semiconductor-type process steps using Au electrodes with a 5 nm Cr under layer as contacts. Structuring these contact electrodes can be easily done with conventional lithography.

As a further embodiment of the invention it is proposed that the resist or another protective layer on top of the graphene (such as e.g. PMMA) is not removed or is given an optimal, for instance conical, shape. This increases the height of the slit on top of the graphene and thereby decreases the angle under which the ss-DNA will pass through the nano-opening in a crossed slit device. Moreover, this has the crucial advantage that a very large shunt current through the ionic buffer solution on top of the graphene layer is avoided, which would overwhelm any small buffer current.

In summary, the invention discloses the fabrication of nano-sequencing devices (solid state nanopores) using block co-polymer self-assembly, particularly of crossed-slit nano-sequencing devices. Said nano-sequencing devices may particularly be comprised of graphene layers.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for manufacturing an apparatus for the processing of single molecules, said method comprising the following steps:
   a) providing a "processing layer" which forms a bottom layer;
   b) depositing a self-assembling resist on said processing layer and letting it self-assemble into a pattern of two phases;
   c) removing selectively one phase of the self-assembling resist;
   d) generating at least one aperture in the processing layer through the mask of the remaining self-assembling resist, wherein steps b), c), and d) are executed at least twice with a first processing layer and a second processing layer, respectively.

2. The method according to claim 1, wherein it comprises the additional step of
   e) removing the remaining self-assembling resist.

3. The method according to claim 1, wherein the second processing layer comprises the first processing layer.

4. The method according to claim 1, wherein the self-assembling resist comprises a block copolymer.

5. The method according to claim 1, wherein an additional layer is deposited at least partially on the processing layer, particularly a non-conductive additional layer.

6. The method according to claim 1, wherein the processing layer is connected to an electrical circuit by which interactions with a molecule passing through the aperture can be controlled.

7. The method of claim 1, wherein an aperture in the second processing layer overlaps a portion of the aperture in the first processing layer and has a perpendicular orientation with respect to the aperture in the first processing layer.

8. The method according to claim 1, wherein the processing layer is pre-treated before the deposition of the self-assembling resist to affect the resulting pattern of phases.

9. The method according to claim 8, wherein the pre-treatment comprises the deposition of a primary resist and its patterning, preferably by optical lithography and/or e-beam lithography, wherein said primary resist forms a trench and the self-assembling resist is deposited solely in the trench.

10. The method according to claim 1, wherein the patterns of the self-assembling resists applied in the first and the second execution are different in alignment and/or geometry.

11. The method according to claim 10, wherein each of said patterns comprises stripes of one phase, wherein the stripes of the different patterns are oblique to each other.

12. The method according to claim 1, wherein the processing layer comprises a non-conductive sub-layer or material and/or a conductive sub-layer or material.

13. The method according to claim 12, wherein the conductive sub-layer or material comprises graphene or a material derived from graphene, preferably in less than five monolayers, most preferably in one monolayer.

* * * * *